United States Patent [19]

Bohlander

[11] Patent Number: 5,731,171
[45] Date of Patent: Mar. 24, 1998

[54] SEQUENCE INDEPENDENT AMPLIFICATION OF DNA

[75] Inventor: Stefan K. Bohlander, Chicago, Ill.

[73] Assignee: Arch Development Corp., Chicago, Ill.

[21] Appl. No.: 96,637

[22] Filed: Jul. 23, 1993

[51] Int. Cl.$^6$ .............................. C12P 19/34; C12Q 1/68
[52] U.S. Cl. ................................ 435/91.2; 435/6
[58] Field of Search ................ 435/6, 91.2; 935/77

[56] References Cited

U.S. PATENT DOCUMENTS 5,043,272  8/1991  Hartley ............................ 435/91.2

OTHER PUBLICATIONS

Nelson et al. PNAS 88: 6157–6161 (1991).
Grothues et al, Nucleic Acid Res 21: 1321–1322 (1993).
Bohlander et al. Am J. Hum Geret Supp 49: 2053 (1991).
Bohlander et al. Genomics 13: 1322–1324 (1992).
Mullis et al, Cold Spring Harbor Symp –p.263–273 (1986).
Baldini et al., "Chromosomal Assignment of Human YAC Clones by Fluorescence *in Situ* Hybridization: Use of Single–Yeast–Colony PCR and Multiple Labeling," *Genomics* , 14: 181–184, 1992.
Bolander et al., "A Method for the Rapid Sequence–Independent Amplification of Microdissected Chromosomal Material," *Genomics* 13: 1322–1324, 1992.
Bohlander et al., "Gene Mapping: Methodology, " *Am. J. Humn. Genet. (Suppl .)*, 49: 365, Oct. 1991.
Breen et al., "YAC Mapping by FISH Using Alu–PCR–Generated Probes," *Genomics* , 13: 726–730, 1992.
Grothues et al., "PCR amplification of megabase DNA with tagged random primers (T–PCR)," *Nucleic Acids Research*, 21 (5) : 1321–1322, 1993.
Lengauer et al., "Fluorescence *in Situ* Hybridization of YAC Clones after *Alu–PCR* Amplification," *Genomics*, 13: 826–828, 1992.
Ludecke et al., "Cloning defined regions of the human genome by microdissection of banded chromosomes and enzymatic amplification," *Nature* , 338: 348–350, 1989.
Sutcliffe et al., "PCR Amplification and Analysis of Yeast Artificial Chromosomes," *Genomics* , 13: 1303–1306, 1992.
Telenius et al., "Degenerate Oligonucleotide–Primed PCR: General Amplification of Target DNA by a Single Degenerate Primer," *Genomics* , 13: 718–725, 1992.

*Primary Examiner*—W. Gary Jones
*Assistant Examiner*—Eggerton Campbell
*Attorney, Agent, or Firm*—Arnold, White & Durkee

[57] ABSTRACT

The present invention is a rapid sequence-independent amplification procedure (SIA). Even minute amounts of DNA from various sources can be amplified independent of any sequence requirements of the DNA or any a priori knowledge of any sequence characteristics of the DNA to be amplified. This method allows, for example the sequence independent amplification of microdissected chromosomal material and the reliable construction of high quality fluorescent in situ hybridization (FISH) probes from YACs or from other sources. These probes can be used to localize YACs on metaphase chromosomes but also—with high efficiency—in interphase nuclei.

24 Claims, 10 Drawing Sheets

PRIMER A   (SEQ ID NO:3)

(SEQ ID NO:3)

(SEQ ID NO:3)

DOUBLE STRANDED DNA

PRIMER A WITH: KNOWN 5´ END    KNOWN 3´ END

DENATURATION OF DNA
(FOR CLARITY ONLY ONE
STRAND (+) IS SHOWN)

ANNEALING OF + STRAND
WITH PRIMER A

STNTHESIS OF - STRAND BY
T7 POLYMERASE
(CAPABLE OF STRAND
DISPLACEMENT SYTHESIS)

DENATURATION
(OMITTING SOURCE
DNA + STRAND AND
UNEXTENDED PRIMER A)

ANNEALING OF – STRAND
WITH PRIMER A

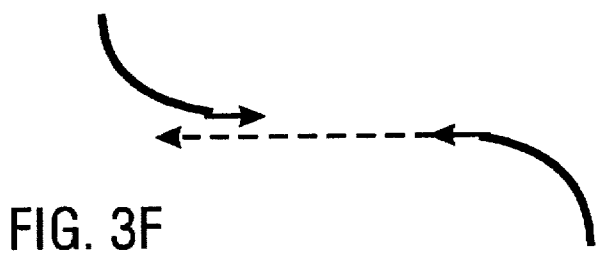

FIG. 3F

SYNTHESIS OF + STRAND
BY T7 POLYMERASE

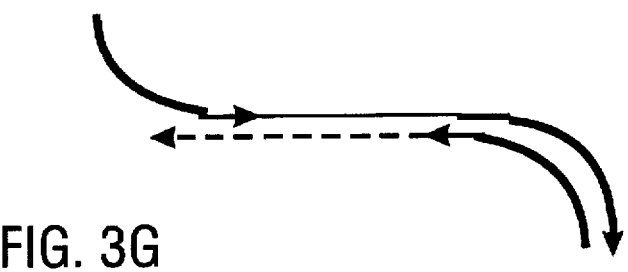

FIG. 3G

THE NEWLY SYNTHESISED + STRAND IS THE SUBSTRATE FOR PCR, SINCE IT IS FLANKED BY KNOWN SEQUENCES (KNOWN PART OF PRIMER A 5′ AND INVERTED COMPLEMENT OF KNOWN PART OF PRIMER A 3′)

KNOWN PART OF PRIMER A 5′

INVERTED COMPLEMENT OF KNOWN PART OF PRIMER A 3′

FIG. 3H

PCR IS NOW PERFORMED WITH PRIMER B, WHICH IS THE KNOWN 5′ PART OF PRIMER A AND AN ADDITIONAL 5 BASES 5′.

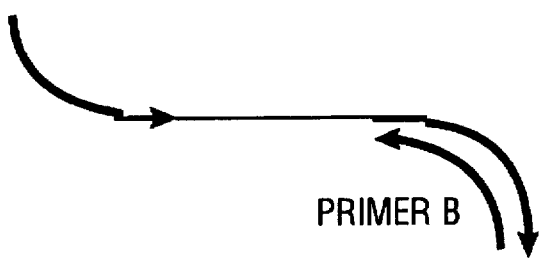

PRIMER B

FIG. 3I

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 17..21
        ( D ) OTHER INFORMATION: /mod_base=OTHER
            / note= "N = A, C, G or T"

( x i ) SEQUENCE DESCRIPTION: SEQ ID NO:1:

TGGTAGCTCT TGATCANNNN N        21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGAGTTGGTA GCTCTTGATC        20

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 8..12
        ( D ) OTHER INFORMATION: /mod_base=OTHER
            / note= "N = A, C, G or T"

( x i ) SEQUENCE DESCRIPTION: SEQ ID NO:3:

TTGATCANNN NN        12

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1..5
        ( D ) OTHER INFORMATION: /mod_base=OTHER
            / note= "N = A, C, G or T"

( x i ) SEQUENCE DESCRIPTION: SEQ ID NO:4:

NNNNNACTAG TT        12

(2) INFORMATION FOR SEQ ID NO:5:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (xi) SEQUENCE DESCRIPTION: SEQ ID NO:5:

T T G A T C A         7

(2) INFORMATION FOR SEQ ID NO:6:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (xi) SEQUENCE DESCRIPTION: SEQ ID NO:6:

A A C T A G T         7

SEQUENCE INDEPENDENT AMPLIFICATION OF DNA

The government owns rights in the present invention pursuant to grants numbers CA49133, CA42557 and CA40046 from the National Institutes of Health and to grant number DE-FG02-86ER60408 from the Department of Energy.

BACKGROUND OF THE INVENTION

1. Field of the Invention

The present invention relates generally to the field of DNA amplification and more particularly to the field of amplifying any stretch of DNA, independent of any prior sequence data or of any sequence requirements for the target DNA.

2. Description of the Related Art

Although the polymerase chain reaction has been one of the most exciting discoveries in recent molecular biological science, allowing the amplification of small amounts of DNA for further analysis, the method has been based on the premise that the sequence to be amplified is flanked by known sequences to which one can hybridize complementary oligonucleotides, called primers.

The use of primers is necessary due to the characteristic of DNA polymerase and Reverse Transcriptase, the enzymes which synthesize new DNA, that these enzymes require at least a short region of double stranded DNA in order to initiate polymerization. The obvious problem has been that in order to design the primers to hybridize to either end of the desired DNA or RNA segment, some sequence information must be known. Therefore, there has been a long felt need in the art, for a method of amplifying segments of DNA or RNA for which no sequence information is available.

One of the first methods of amplification of unknown sequences was the "linker ligation" approach which has been applied to both microdissected chromosomes (Lüdecke et al., 1989), and to the analysis of yeast artificial chromosome (YAC) DNA (Sutcliffe et al., 1992). In this approach the DNA to be amplified was first digested with a restriction enzyme, usually an enzyme with a four base recognition sequence. After inactivation of the restriction enzyme, a known sequence (either a vector or a synthetic linker) was ligated to the fragments from the restriction enzyme digest. The DNA could then be amplified by PCR, using primers that were complementary to the sequence of the linker or vector.

Unfortunately, this method has several limitations. For example, sequence-independent amplification is not actually achievable with this method. Sequences that do not contain the recognition sequence of the restriction enzyme at appropriately spaced intervals are not amplifiable. For example, the linker, and hence the restriction site must be present on both ends of the sample DNA for the PCR amplification. Therefore, two of the restriction enzyme recognition sites must exist within a limited distance of each other for the linker technique to work. Also, due to the extensive manipulations of the DNA that are necessary to attach the known sequences to either end of the fragments, the method is cumbersome and time consuming, especially when applied to small quantities of DNA such as microdissected chromosomal pieces.

Another, more restrictive method to achieve amplification of random sequences from human DNA is the use of inter-ALU PCR (more generally known as inter repetitive element PCR). This method relies on the presence of appropriately spaced and oriented ALU repetitive elements or other repeated sequences. The method gives inconsistent results with low complexity DNA sources such as YACs, cosmids or phage because of the low incidence of these repeat sequences. Other inconsistencies arise because the repeated sequences do not occur uniformly throughout the genome, or a sequence of interest may occur in an area in which the necessary repeated sequences are rare or absent. Another major limitation of this method is that it is species specific. For example, the use of this method is restricted to DNA of the species from which the repetitive elements derive and for which the primers were constructed.

Another attempt to achieve sequence-independent amplification has been described by Telenius et al. (1992). In this method, the first rounds of the PCR amplification have a low primer annealing temperature of around 30° C. The primer used consists of a random hexamer that is flanked on the 3' side by a defined hexamer and on the 5' end by a defined sequence that also may contain a restriction enzyme site for convenient cloning of the products. Because the primer does not have a random 3' end, but a defined hexamer, there are certain sequence requirements for the template. In other words, in order for the primer to anneal to the target DNA, the target sequence must match relatively closely to the 3' end of the primer. Therefore, there are a limited number of sequences which will be amplified by this method.

The inadequacy of the Telenius method is demonstrated when this method is applied to DNA sources of limited complexity such as YACs, cosmids or phage inserts. The resulting product is not seen as a smear on a ethidium bromide stained agarose gel (as occurs with randomly amplified DNA), but results in distinct bands, indicating that the hybridization occurs only at relatively few discrete sites and thus sequence independent amplification is not achieved.

Another problem with the method reported by Telenius et al. (1992) arises from the use of Taq polymerase in the initial low annealing temperature reactions. This enzyme is active and stable at the higher temperatures necessary for the higher stringency PCR reactions, but is relatively inactive at the low temperatures required for the initial reactions. In fact, PCR reactions that are performed with Taq polymerase are sometimes held overnight at room temperature after automatic cycling because of the negligible activity of the enzyme under those conditions. Therefore, there exists an immediate need for an efficient method of amplifying DNA that is: (1) sequence independent; (2) applicable to DNA from any species; (3) useful for amplifying any area of a DNA sample; and (4) capable of amplifying extremely small amounts of DNA.

SUMMARY OF THE INVENTION

The present invention seeks to overcome these and other drawbacks inherent in the prior art by providing a method of amplifying DNA segments independent of the sequence. By independent is meant that the DNA segment to be amplified does not have to be derived from any particular species or organism. The DNA segment also does not have to contain any particular restriction enzyme recognition sequences, nor any repetitive sequences. It is understood that the present invention encompasses sequence independent amplification of DNA from any source, such as human, animal, plant, yeast, viral or prokaryotic DNA.

It is understood that the basic steps in amplification are comprised of a heat denaturation step in which the sample DNA is melted to a single stranded condition which is necessary for the annealing of the small primer. This is followed by a lower temperature incubation in which the primer and sample form hybrid duplexes. The next step is an incubation period during which the DNA polymerase extension reaction occurs. This reaction is generally at an intermediate temperature, for example higher than the annealing temperature and lower than the melting temperature. This cycle of at least three temperatures is then repeated for the appropriate number of cycles. Generally, there is one more step in which the reaction is incubated for a few minutes at or near the extension reaction temperature to complete any nascent reactions.

The initial primer used in the method of the present invention is designated primer A. The primer A, is comprised of from about 4 to about 8 and preferably about 5 random nucleotides at its 3' end and from about 10 to about 30 and preferably from about 15 to about 20 nucleotides of defined sequence at its 5' end. An example of a primer A is the sequence designated SEQ ID NO:1. The random nucleotides can be any of the nucleotides, for example G, A, T or C in any order. It is understood that the alphabetic designations represent: G for guanylic, A for adenylic, T for thymidylic and C for cytidylic nucleotides. The primer A added to the DNA mixture theoretically may contain all combinations of these nucleotides in every position of the random portion of the primer. Thus, the 3' end of the primer A will be complementary to random sites throughout the target DNA segments.

The defined sequence can be any sequence that would constitute a good PCR primer. For example, there should be no obvious self-homologies, no runs of the same nucleotide, and they should not be overly G:C or A:T rich. For example, a primer that contains self-homologies, or sequences in one region that are complementary to sequences in another region of the primer will form internal hairpin duplexes and would thus be unavailable to hybridize with the sample DNA. Also, since the G:C pairing involves 3 hydrogen bonds and the A:T pairing involves only 2 hydrogen bonds, a primer comprised of a disproportionately high content of the nucleotides G or C, singly or in combination, would have a higher melting temperature than a primer that was comprised of a higher content of A and T. Of course, the importance of the defined sequence region of primer A is that it is known. Within the limits mentioned above, any defined sequence will work, and therefore any primer whose defined sequence contains nucleotide bases other than those contained in SEQ ID NO:1, for example, would still be encompassed by the present invention.

The melting temperature of the entire primer should preferably be more than about 60° C. in standard PCR buffer and the melting temperature of the defined nucleotide sequence should be about 40° C. to 50° C. and preferably about 45° C. It is well known to those of skill in the art that the optimal temperatures for each step in the PCR are determined (usually empirically) by the size of the sample DNA or RNA to be amplified and by the size and sequence of the primer. For example, simple formulas for determining the melting temperature of a perfectly matched duplex based on the G:C content are well known in the art.

One may also desire to incorporate one or more restriction enzyme sites for subsequent cloning of the amplified products. For example, the use of particular restriction enzymes is well known in the art. The restriction enzyme is normally chosen to be compatible with the vector of choice for cloning the PCR product. For example, popular vectors such as PBR 322, the pGem or PUC series of plasmids contain certain specific restriction enzyme recognition sites in their polyclonal regions. The recognition sequence included in the primer of the present invention would then be one that is compatible with the sites in the chosen vector.

In the method of the present invention, the DNA to be amplified is first denatured by heating to between from about 90° C. to about 97° C., and preferably to about 94° C. for about one to five minutes and preferably for about two minutes. During this step, an oligonucleotide primer designated primer A may also be present. The primer may be added to the reaction mix containing the DNA to be amplified before the heat denaturation or at any time during the denaturation step.

After the heat denaturation, the mixture is cooled to between about 4° C. and about 13° C. which allows the random segments of the primers A to anneal to their complementary sequences. As an example, if the 3' end of the primer A was comprised of 5 random nucleotides, there would be $4^5$ or 1,024 different sequences in the random segment of primer A for that particular amplification. The complements of these sequences occur in both orientations at random throughout the denatured DNA segments. By both orientations is meant that priming would occur on both strands of the melted duplex which is to be amplified.

After the annealing step, DNA polymerase is added and the temperature is increased gradually over about a one to about an eight minute period and preferably over about a three minute period to from about 25° C. to about 40° C. and preferably to about 37° C. and held at that temperature for between about one to about eight minutes. The preferred DNA polymerase used in this step is a heat sensitive enzyme that has primer displacement activity and is without exonuclease activity. The polymerase used is preferably T7 DNA polymerase and more preferably a modified T7 DNA polymerase (Sequenase Version 2.0; United States Biochemicals). Primer displacement activity means that when the polymerase is moving along the DNA and encounters another primer annealed to the DNA, the second primer will be displaced and the polymerase reaction will proceed. This trait results in longer polymerization products.

This initial reaction will result in DNA segments of various lengths which are comprised of the defined sequence of primer A at their 5' ends. This reaction mix is then reheated for denaturation as before and re-annealed. For each repeat of this polymerase reaction, fresh enzyme must be added, as the initial reactions are done with a polymerase which is destroyed by the heat necessary to denature the DNA. The cycle is repeated for a total of one to eight times, preferably four times as above, again with fresh enzyme added for each cycle. Because, during the second round, the oligonucleotide primer A will also anneal to products of the first reaction, some of the products of this second cycle will be comprised of the DNA segment to be amplified, flanked by the defined sequence of primer A on their 5' ends and the reverse complement of that defined sequence on their 3' ends.

The final reaction products of the initial cycles of amplification are then diluted into buffer, preferably from about 1 to about 100 fold and most preferably about ten-fold. For practical reasons, the initial reactions are generally performed in relatively low volume. This may be especially necessary when the sample DNA is present in small amounts as in microdissected chromosomes and in YACs isolated from pulsed field gels. The initial volume may be as low as 2 μl. At each new round, from about 0.5 to about 2.5 μl may be added. Depending on how many cycles are run, the final volume after these initial reactions may typically be about 7 µl. It is understood that these volumes may vary widely depending on the particular application and that higher or lower reaction volumes are encompassed by the present invention.

After the initial reactions, the final reaction mix is diluted with buffer for to adjust conditions for the PCR. The dilution serves at least a two-fold purpose. Since the optimal buffer for the T7 DNA polymerase is different from the optimal buffer for the Taq polymerase, the presence of a relatively small mount of T7 buffer will not interfere with the Taq polymerase reaction. The dilution also serves to lessen the competitive hybridization of primer A as it will be present in much lower concentration after the dilution. It is understood that the mount of dilution at this step is chosen empirically, and for convenience in the practice of the method, as for example, ten-fold dilutions are easily calculated and executed. It is understood that any dilution factor that is compatible with a particular set of reactions is acceptable and is encompassed by the present invention.

A different oligonucleotide primer, primer B, is used for the PCR reactions. The 3' end of Primer B is comprised of the defined nucleotides that comprise the 5' end of primer A. Primer B may also be comprised of an additional region of from about 5 to about 15 defined nucleotides at its 5' end. In the initial cycles of this method as described in the paragraphs above, low temperatures for the annealing and extension reactions are chosen because there are stretches of only about 5 nucleotides that hybridize with the DNA to be amplified. However, the products of these early cycles are comprised of the target DNA flanked by the approximately 15 to 20 bases of defined sequence of primer A and its reverse complement. These flanking sequences hybridize with the complementary portion of primer B. This longer stretch of hybridization allows the subsequent reactions to be done at a higher temperature. Therefore, the T7 polymerase is no longer necessary and a polymerase that is stable at high temperature, such as, preferably Taq DNA polymerase may be used.

The reaction is heated to between about 92° C. and about 99° C. and more preferably to about 94° C. for from about thirty seconds to about two minutes and preferably for about forty five seconds to denature the DNA. Primer B may be added to the reaction before or at any time during the heat denaturation. The mixture is then cooled to from about 40° C. to about 45° C. to allow primer B to anneal to the amplified DNA from the initial cycles.

The temperature is then increased over about a one minute to about a six minute period and preferably over about a two minute period to from about 70° C. to about 75° C. and preferably to about 72° C. and held there for from about one to about five minutes. This cycle is repeated about 5 times. It is not necessary to add fresh enzyme for each cycle, as the Taq DNA polymerase is not completely denatured by the heat step. These cycles are the low stringency cycles. When the extra defined bases have been added to the 5' end of primer B, these extra bases will have been added to both ends of the amplification products in reverse complement. Therefore, after the low stringency cycles, the primer B will have a longer hybridization region and the hybridized duplexes will be stable at higher temperatures. High stringency cycles further reduce competitive annealing of primer A.

The high stringency cycles are run as follows: the reaction temperature is increased to from about 90° C. to about 97° C. and preferably to about 94° C. and held for about 30 seconds to about two minutes and preferably for about 45 to about 50 seconds. The temperature is then decreased to about 45° C. to about 65° C. and preferably to about 56° C. and held for about thirty seconds to about two minutes. The temperature is then increased to about 70° C. to about 75° C. and preferably to about 72° C. and held for about one minute to about five minutes and preferably for about two minutes. This cycle is repeated about 30 to about 35 times and preferably about 30 to 33 times. The reaction is then held at about 72° C. for about 7 minutes to complete any nascent polymerizations.

It is understood that when one adds enzyme or buffer to the reactions of the present method, that the enzyme and buffer may be mixed with the other necessary reaction components. These necessary reaction components may include, but are not limited to bovine serum albumin, $MgCl_2$ in a concentration of from about 5 mM to about 20 mM final concentration, the four deoxynucleotide bases, dATP, dGTP, dTTP and dCTP, and purified water, for example distilled, deionized or ultrafiltered. The buffers to be employed may be comprised of components such as Tris HCl at a pH of from about 7.0 to about 9.0, $MgCl_2$, NaCl and DTT (dithiothreitol). Buffers may also include KCl and gelatin. The composition of buffers for the PCR are well known to those of skill in the art, and the concentration of certain components, $MgCl_2$ for example, is often determined empirically for each reaction.

It is also understood by those who practice the art that the temperatures, incubation periods and ramp times of the PCR technique may vary considerably without significantly altering the results. These minor variations in reaction conditions and parameters are also included within the scope of the present invention.

The products of the above reactions may then be run on an agarose or acrylamide electrophoresis gel and preferably on a 1.5% agarose gel. After staining with ethidium bromide, the products of random, sequence independent amplification will appear as a smear.

In a certain embodiment, the present invention encompasses a method for amplifying DNA, independent of the sequence of the DNA, comprising the steps of:

(a) adding about 0.5 µl of a DNA sample to about 4 µl of an amplification reaction mixture including 40 mM Tris HCl (pH 7.5), 10 mM $MgCl_2$, 50 mM NaCl, 5 mM dithiothreitol, 50 µg/ml bovine serum albumin, 300 µM dATP, 300 µM dGTP, 300 µM dCTP, 300 µM dTTP, and between about 1.25 µM and about 3 µM of a first primer having the sequence of SEQ ID NO:1;

(b) denaturing said DNA by heating said reaction mixture to a temperature of between about 94° C. and about 97° C. for about 2 minutes, then cooling said reaction mixture to a temperature of between about 4° C. and about 13° C., thereby allowing said first primer to anneal to said denatured DNA to form a DNA-primer hybrid;

(c) contacting said DNA-primer hybrid with about 0.5 units of T7 DNA polymerase diluted in reaction buffer, increasing the temperature to about 37° C. over about a 5 minute period and maintaining at this temperature for between about 2 minutes and about 8 minutes, thereby forming an amplified DNA product;

(d) repeating steps (a) through (c) between one and about three times using an additional sample of T7 DNA polymerase each time;

(e) adding to the amplified DNA product from step (d) between about 54 µl and about 90 µl of a PCR reaction mixture including 6.6 mM Tris HCl (pH 9.0), 0.25 mM MgCl$_2$, 55 mM KCl, 0.01% W/V gelatin, 77 µM dATP, 77 µM dGTP, 77 µM dCTP, 77 µM dTTP, about 2.5 units of Taq DNA polymerase and between about 2.2 µM and about 1.5 µM of a second primer having the sequence of SEQ ID NO:2, and subjecting said amplified DNA product to further rounds of amplification by PCR using about 5 low stringency PCR steps followed by between about 30 and about 33 high stringency PCR steps.

The present embodiment can be further described as a method wherein said further rounds of amplification by low stringency and high stringency PCR comprise the steps of:

(a) denaturing said amplified DNA by heating to a temperature of about 94° C., then cooling said denatured amplified DNA to a temperature of between about 42° C. and about 44° C. to form a DNA-second primer hybrid;

(b) increasing the temperature to 72° C. over about a 4 minute period and maintaining at this temperature for about 3 minutes to form further amplified DNA;

(c) repeating steps (a) and (b) about five times;

(d) denaturing said further amplified DNA by heating to a temperature of about 94° C., then cooling said denatured further amplified DNA to a temperature of about 56° C. to form further DNA-second primer hybrids;

(e) increasing the temperature to 72° C. and maintaining at this temperature for about 2 minutes to form further amplified DNA; and (f) repeating steps (d) and (e) between about 30 and about 33 times.

A certain embodiment of the present invention is a method of fluorescence in situ hybridization analysis of chromosomes. First, a chromosomal DNA sample of interest is obtained. This sample may be a Yeast Artificial Chromosome (YAC) chromosomal insert, a sample of microdissected chromosome, a cosmid DNA insert, a plasmid insert or a phage insert, lambda phage for example. The YAC may be isolated from the other yeast chromosomes on a pulsed field electrophoresis gel. Once obtained, the DNA is amplified by the method described above. The amplified DNA can then be labeled by a further PCR which contains a labeled nucleotide base which will be incorporated into the amplified product. The label may include, but is not limited to biotin, Spectrum-Orange or Spectrum-Green.

The labeled DNA is then hybridized to a chromosome preparation such as interphase or, preferably, metaphase spreads. In metaphase spreads, the chromosomes are shortened and thickened and are more easily visualized and identified. Hybridization with the labelled probe allows one to determine the particular chromosome and the position on the chromosome from which the amplified probe was derived. The amplified, labeled probe may also be hybridized to interphase nuclei in order to determine the number of hybridization sites in the nucleus. The hybridized probes which are labeled with biotin can be visualized with fluorescein-isothiocyanate conjugated avidin under a fluorescence microscope. Probes labeled with Spectrum-Orange or Spectrum-Green are directly visualized by fluorescence microscopy.

In a certain embodiment, the present invention is a pair of primers for use in DNA amplification. The first primer comprises a region of about 4 to about 8 random bases at the 3' end and about 15 to about 20 defined bases at the 5' end. This primer is further characterized by the ability of its random sequence to hybridize to any DNA sequence at a temperature of between about 4° C. and about 13° C. The second primer is between about 15 and about 28 nucleotides in length and has at its 3' end the 15 to 20 nucleotide long defined sequence of the first primer. The second primer may also contain additional bases to facilitate the method of amplification, particularly in relation to the high stringency PCR step. The second primer may also contain a restriction enzyme recognition site to facilitate the subcloning of the PCR product into a vector of choice or a stretch of CUA repeats to allow cloning by the "Clone Amp" protocol (BRL).

An example of the first primer, also known as primer A, is the sequence 5'-TGGTAGCTCTTGATCANNNNN-3', SEQ ID NO:1. An example of the second primer, also known as primer B, is the sequence 5'-AGAGTTGGTAGCTCTTGATC-3', SEQ ID NO:2. The underlined portion of SEQ ID NO:2 is contained in the defined sequence of SEQ ID NO:1.

Kits for use in the sequence-independent amplification of DNA are also contemplated as another embodiment of the present invention. Such kits might comprise a container, for example a plastic box with a hinged lid and containing a structure for holding individual vials or tubes.

One of the said tubes may contain an oligonucleotide primer, designated as primer A. This first primer would comprise from 3 to about 6 random nucleotides at the 3' end and from about 15 to about 20 nucleotides of defined sequence at the 5' end. An example of a primer A which may be included in the kit is the sequence designated SEQ ID NO:1. A separate tube may contain a second oligonucleotide primer, designated primer B, of between about 15 and about 28 nucleotides in length having at its 3' end a sequence in accordance with the defined sequence of said first primer, or primer A. An example of a primer B would be the sequence designated SEQ ID NO:2. The primers could be provided in a buffer solution, such as for example TE (10 mM Tris HCl pH 7.5, 1 mM EDTA) at a concentration of for example 10 to 100 times the recommended final reaction concentration of the individual primers. The oligonucleotide primers could also be provided in a lyophilized, crystalline form to be redissolved by the user as needed.

Another vial or tube in the kit would contain the DNA polymerase to be used in the initial reactions of the sequence independent amplification. Examples include T7 DNA polymerase, Klenow Fragment, DNA Pol III or a modified T7 DNA polymerase. A fourth vial or tube would contain a heat stable DNA polymerase suitable for use in PCR, for example, Taq DNA polymerase. The two enzymes could be provided in a stabilized buffer. The enzymes might also be provided in a lyophilized, crystalline form to be redissolved by the user.

Another vial or tube in the kit would contain a buffer for use in the reaction with the first DNA polymerase. This buffer could be provided in a 10 times final concentration (10x). For example, a buffer solution might contain 0.4M Tris HCl (pH 7.5), 0.5M NaCl, 50 mM dithiothreitol and 500 µg/ml bovine serum albumen. Yet another vial or tube provided in the kit would contain the buffer to be used in the PCR reactions, designated buffer B. This buffer might also be provided in a 10x concentration. For example, the buffer might contain 66 mM Tris HCl (pH 9.0), 0.55M KCl and 0.1% (w/v) gelatin. Another tube in the kit may contain a mixture of deoxynucleotides, for example a mixture of dATP, dTTP, dCTP and dGTP. This mixture is generally designated as a dNTP solution. Still another tube or vial might contain a solution of MgCl$_2$.

It is understood that the buffers designated buffer A and buffer B might also contain the dNTPs, and/or the appropriate primer in the buffer solutions and in such a case, the separate dNTP or primer vial or tube would not be necessary. The buffer tubes might also contain $MgCl_2$, however, since the optimal concentration of $MgCl_2$ may vary for different reactions, it is generally provided separately.

The kits may be designed to be stored in a freezer at a temperature, for example of from −20° C. to about −80° C. When the $MgCl_2$ is provided in a separate tube, it may be stored under refrigeration at 4° C. for example. Also provided in the kit would be a manual with detailed instructions for the use of the kit and a description of the materials contained in the kit. The kit may contain enough materials for about 100 reactions and would provide a convenient tool for practicing the method of the present invention.

The use of the kit to obtain reliable FISH signals from YACs will allow new ways of screening for the presence of common chromosomal translocations in a variety of human tumors. Since the sequence independent amplification as disclosed herein is a simple procedure, it is easy to run control reactions or to amplify several chromosomal regions at the same time thus reducing the time and effort required to obtain results. The danger of contamination is also minimized because the number of steps and manipulations is greatly reduced in comparison to the traditional methods.

The sequence independent amplification method will not only allow the rapid construction of band specific painting probes for any chromosomal region, but the method can also be used to microdissect and amplify unidentifiable chromosomal regions or marker chromosomes in abnormal karyotypes. The method should therefore become a valuable tool in cytogenetic diagnosis.

BRIEF DESCRIPTION OF THE DRAWINGS

FIG. 2 is contained on six panels, FIG. 2A, FIG. 2B, FIG. 2C, FIG. 2D, FIG. 2E, and FIG. 2F, and is a short, diagrammatic representation of sequence independent amplification. FIG. 2 contains parts A–F. FIG. 2C, and FIG. 2D is designated SEQ ID NO:3. Primer B in FIG. 2F is a truncated representation of the full sequence of the actual primer B (SEQ ID NO:2) used in the development of the invention.

FIG. 2A represents the double stranded target DNA before denaturation and the primer A, represented in the figure by SEQ ID NO:3.

FIG. 2B represents the annealing of the random portion of primer A, represented in the figure by SEQ ID NO:3, to a single strand of the denatured DNA.

FIG. 2C represents the replication of the single strand DNA by DNA polymerase.

FIG. 2D represents the second cycle of replication in which the random portion of primer A, represented in the figure by SEQ ID NO:3, anneals to the product of the first reaction.

FIG. 3 is contained on nine panels, FIG. 3A, FIG. 3B, FIG. 3C, FIG. 3D, FIG. 3E, FIG. 3F, FIG. 3G, FIG. 3H, and FIG. 3I, and is a more detailed illustration of the strategy of sequence independent amplification.

FIG. 3F is a representation of the annealing of primer A with the product of the first reaction.

FIG. 3G is a representation of the synthesis of a new DNA product which is flanked by the sequence of primer A on one end and the reverse complement on the other end.

FIG. 3H is a representation of the product of the reaction from FIG. 3G.

FIG. 3I is a representation of the annealing of primer B to the product represented in FIG. 3H.

FIG. 4 is contained on four panels, FIG. 4A, FIG. 4B, FIG. 4C, and FIG. 4D, and is a photograph of a partial trypsin-Giemsa banded metaphase cell.

FIG. 5 is contained on two panels, FIG. 5A and FIG. 5B, and is a photograph of DAPI stained metaphase and interphase cells following hybridization of the YAC Not-42 probe. Arrows point to the two chromosome 21 homologues. All photographs were single exposures taken on a Zeiss standard 16 microscope equipped with epifluorescence using Fuji Chrome 400 film. For the photographs in FIG. 5D and FIG. 5C, a dual band pass filter (Chroma Technology Corp., filter set #51001) was used.

FIG. 6 contains parts A–B. The products were labeled with biotin by secondary PCR and then treated with DNAse I as described herein. FISH was performed to normal metaphase spreads. The signal was detected by FITC conjugated avidin. Two separate gray scale images were taken with a CCD camera. One with a filter set for the DAPI stain and the other with the filter combination for the FITC signal.

Figure 6A:
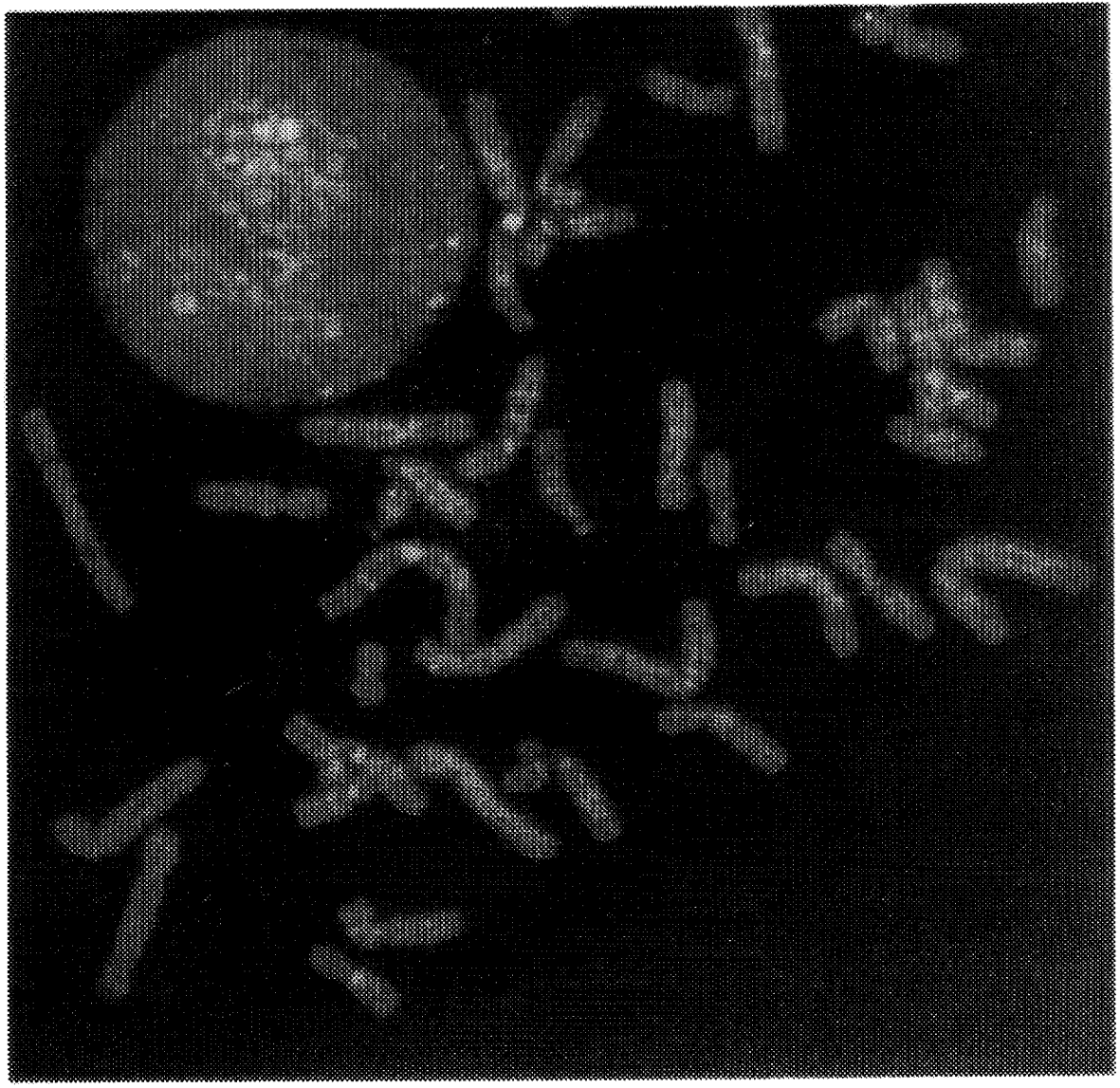
FIG. 6 is contained on two panels, FIG. 6A and FIG. 6B, and represents 100 pg to 1 ng of cosmid DNA amplified by SIA.
Figure 6B:
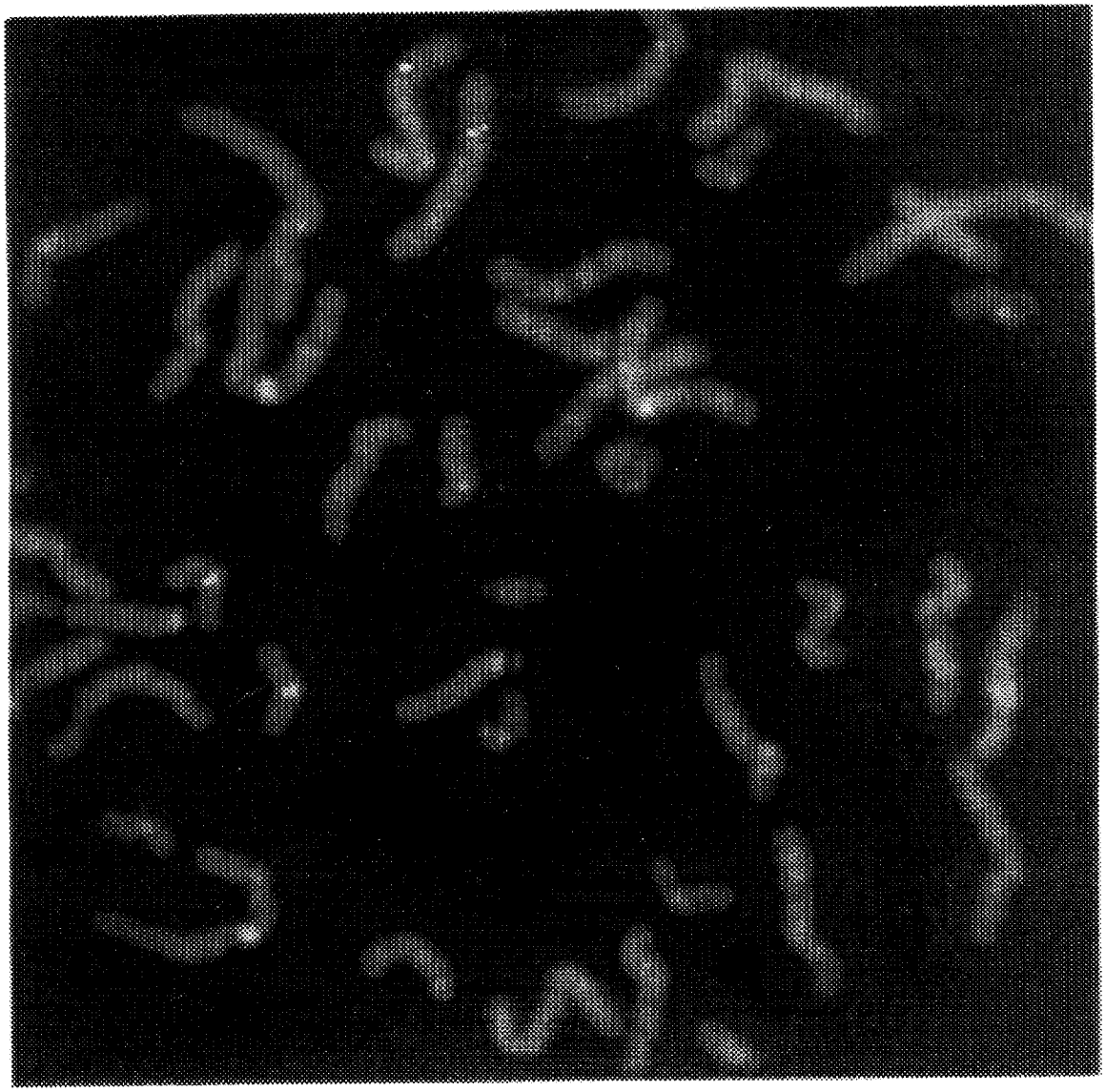

The grayscale images were then merged so that the signals would appear as white dots on the cormomosems which show a gray DAPI banding pattern. One cosmid was from chromosome 21 (FIG. 6A) and the other mapped to chromosome 5q31 (FIG. 6B). Both cosmids had inserts of approximately 40 kbp.

Figure 7:
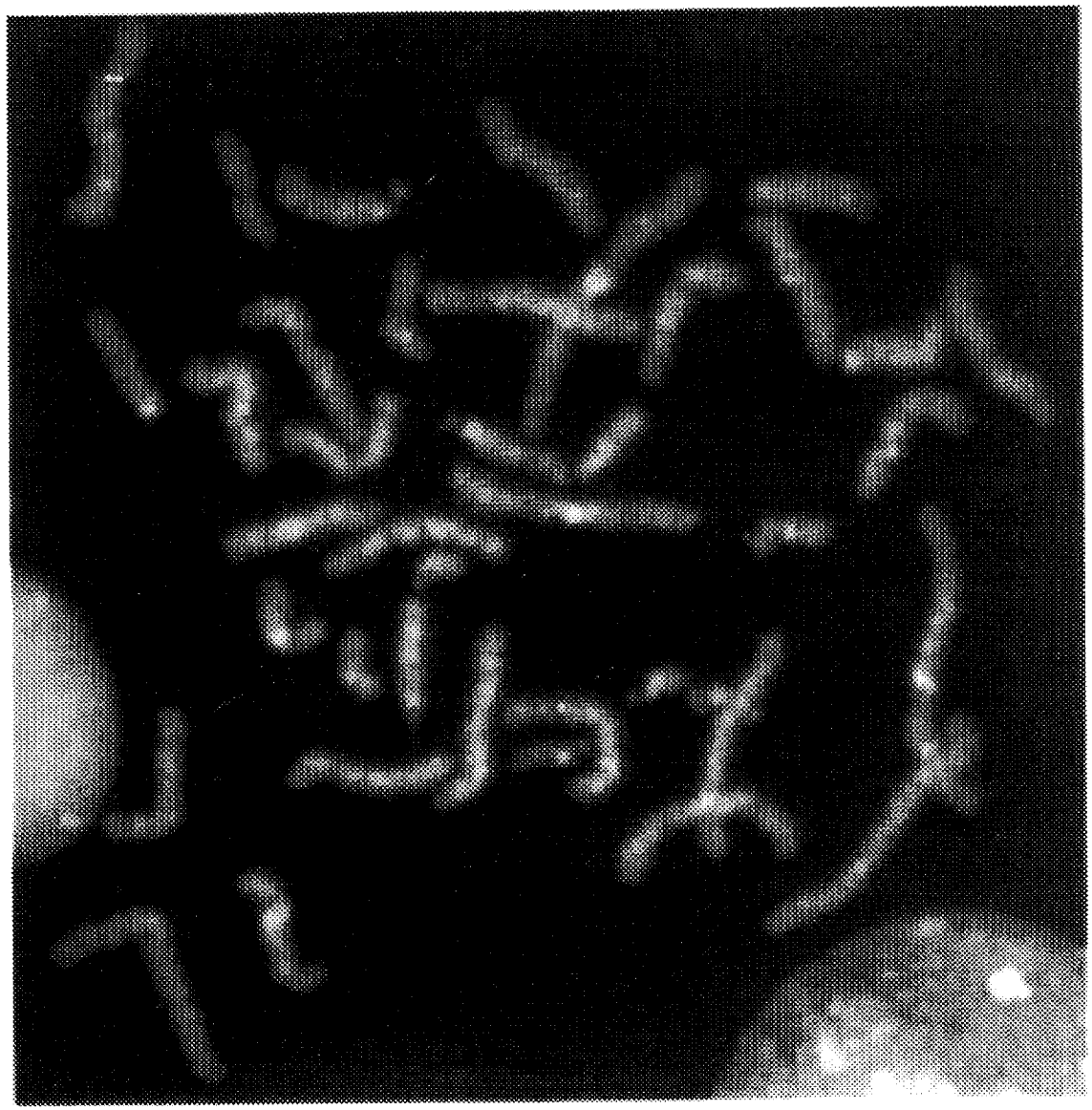

FIG. 7 represents 100 pg to 1 ng of total phage DNA amplified by SIA. The products were labeled and hybridized in the same manner as described in FIG. 6A and FIG. 6B. The photographs were obtained in the same manner. Clear signals on both homologues of chromosome 5 band q31 are observed. The human insert of the phage was approximately 15 kbp.

DETAILED DESCRIPTION OF THE PREFERRED EMBODIMENTS

One embodiment of the present invention is a simple, efficient method by which microdissected DNA can be amplified directly in the collection container in a few hours. The procedure involves several initial rounds of DNA synthesis with T7 DNA polymerase using a primer that is comprised of a short random sequence at its 3' end and a defined sequence at its 5' end, followed by PCR amplification with the defined sequence of the first primer as the primer for the PCR. The resulting products can, for example be biotinylated and used for fluorescence in situ hybridization (FISH) to confirm their chromosomal location. As few as seventeen dissected chromosomal regions provide sufficient material for a specific FISH signal on the appropriate band of metaphase chromosomes. The present inventors have obtained a chromosome 6q25-qter specific painting probe in this way.

The construction of libraries from microdissected chromosomal bands is an elegant way to obtain DNA probes from regions of particular interest. These probes will be especially valuable in the effort to construct detailed maps of the human genome. However, the applicability of this approach has been restricted by the time consuming and technically difficult process of sequence independent amplification of DNA from the microdissected material. Traditionally the DNA from 20 to 30 microdissected chromosomal bands is collected in a small droplet. The DNA is then subjected to various manipulations before it is used for PCR amplification. These manipulations include phenol/chloroform extractions, restriction enzyme digestion and ligation to a vector or linker. All these steps are performed in very small volumes on the stage of a microscope with specialized equipment (Lüdecke et al. 1989; Kao and Yu 1991).

An attempt to simplify the method of sequence independent amplification was reported by the inventor in an abstract (Bohlander, et al., 1991). However, the method described in this report was subsequently shown not to be effective. Therefore there still exists an immediate need for a method of amplifying minute amounts of DNA independent of the sequence or the origin of the DNA.

Yeast artificial chromosomes (YACs) are ideal vectors for the detailed mapping of large stretches of DNA (Burke et al., 1987). One of the main disadvantages of the YAC cloning system is that there have been no methods available to purify the YAC DNA in large quantities. High molecular weight DNA can be prepared from yeast clones carrying YACs and the YACs can be isolated on a pulsed field gel. This approach, however, yields only very small amounts of pure YAC DNA. This is a major disadvantage because many important uses of these large inserts, e.g. screening cDNA libraries or FISH analysis, require larger amounts of purified YAC DNA.

Several strategies have recently been proposed that allow better and sometimes easier preparation of YAC DNA for FISH analysis. One of these approaches is the use of Alu-PCR (Nelson et al., 1989) to amplify certain fragments of the YAC that lie between appropriately oriented Alu-repeat elements, and the subsequent use of the amplified fragments for FISH analysis (Baldini et at., 1992; Breen et al., 1992; Lengauer et at., 1992). Another approach is to isolate the YAC DNA after separation by pulsed-field gel electrophoresis, digest the DNA with a frequent cutting enzyme and ligate a linker-adapter to the restriction fragments. The fragments can then be amplified by PCR using primers for the known sequence of the adapter-primer and the resulting products can be labeled and used for FISH analysis (Sutcliffe et al., 1992). Another recent attempt has been made using a partially degenerate primer (Telenius et al., 1992); however this method is generally unacceptable because the DNA prepared by this method does not produce good fluorescence in situ hybridization (FISH) signals.

Another embodiment of the present invention is the use of a different strategy to amplify the YAC DNA in a sequence-independent manner after its isolation in a pulsed-field gel (Boblander et al., 1991, 1992). This sequence-independent amplification (SIA) method requires no prior purification of the DNA, restriction enzyme digestion or ligation. It also has no a priori sequence requirements for the DNA that is to be amplified, in contrast with the linker-adapter method which requires certain restriction sites to be present. This results in a substantial improvement in the speed of probe preparation and in the quality of the FISH signal over earlier strategies.

The ability to obtain such reliable FISH signals from YACs will allow new ways of screening for the presence of common translocations in a variety of human tumors. One should be able to detect translocations that split YACs or that bring different YACs together in interphase nuclei, thereby obtaining information even from tumors with a very low mitotic index. The large regions of DNA that are detected by such YAC probes provide better signal intensities than cosmids or cosmid contigs. Cosmid contigs are sets of cosmids that partially overlap. Theoretically, cosmid contigs can span long stretches of DNA. Commercially available cosmid contigs are typically cloned with one probe and span less than 80 kb. The advantage of better signal intensity, together with the ability to use a simple epifluorescence microscope should lead to the introduction of YACs as routine FISH probes in clinical cytogenetics and pathology laboratories. Moreover, a larger portion of a chromosome can be screened for the presence of translocation breakpoints or other rearrangements by using YACs with large inserts as FISH probes.

The method will also help in the rapid physical mapping of YACs to metaphase chromosomes as well as in interphase nuclei. One would also be able to detect YACs that have chimeric inserts, a common problem in many YAC libraries. Because the method does not depend on repetitive elements specific to any particular species to achieve amplification, it will also be useful for the YAC mapping of the genetic material of experimental animals such as the mouse or Drosophila.

Sequence-independent Amplification (SIA)

The SIA method allows the in-vitro amplification of DNA without knowledge of the nucleotide sequence of the DNA to be amplified. The method is based on the use of a special primer (Primer A) and modified T7 DNA polymerase (Sequenase Version 2.0; United States Biochemicals) in the first amplification rounds. Then a PCR reaction with a second primer (Primer B) and Taq DNA Polymerase is used in the remaining rounds.

Definition of Primer A:

Primer A has a random 3' end, i.e. 3 to 6 positions that can be occupied by any base and a defined 5' end of 15 to 20 nucleotides. The most 3' nucleotide may also be fixed to facilitate oligonucleotide synthesis.

Figure 1:
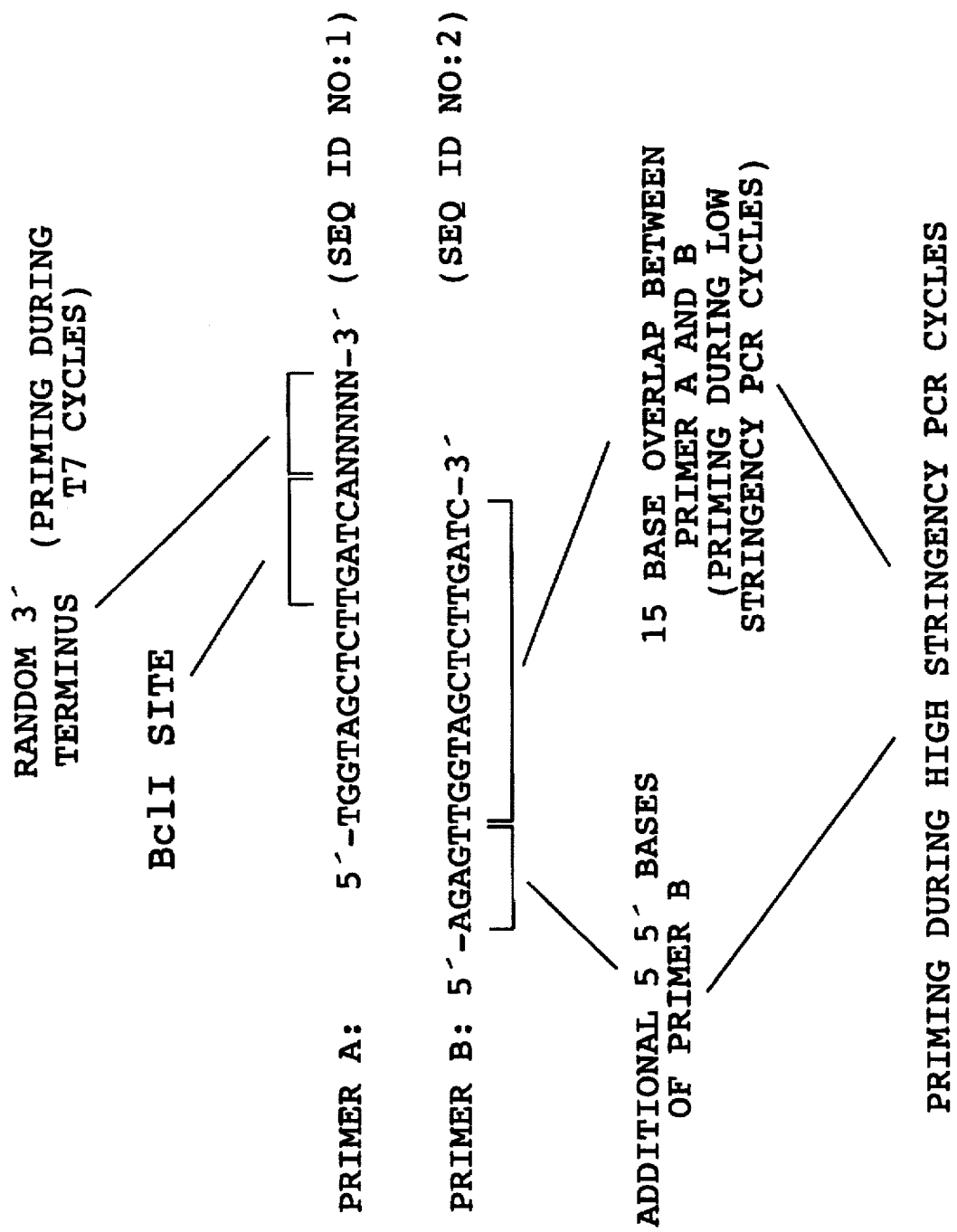
FIG. 1 is a diagram to illustrate which parts of the two primers are important at different steps in the procedure of sequence independent amplification. In the figure, primer A is designated SEQ ID NO:1. Primer B is designated SEQ ID NO:2.

Definition of Primer B:

Primer B has at its 3' end the sequence of the defined region of primer A and may have an additional 5 to 8 defined bases at its 5' end. The defined sequence may be any sequence that would constitute a good PCR primer (i.e. no obvious self-homologies, no runs of the same nucleotide, and not overly G:C or A:T rich). The melting temperature of the entire primer should preferably be more than 60° C. in standard PCR buffer and the melting temperature of the 15 to 20 defined nucleotides that correspond to primer A should be about 45° C. The sequence may also incorporate some restriction enzyme sites for subsequent cloning of the amplified products (e.g. the BclI site in FIG. 1).

Rationale for choosing T7 DNA polymerase

Genetically modified T7 DNA polymerase was chosen for the first rounds because it is active at low temperatures, has a high degree of processivity, has the capability of strand displacement synthesis and lacks exonuclease activity (United States Biochemicals). These properties enable the T7 DNA polymerase to synthesize long stretches of DNA at the relatively low temperatures at which the primer-DNA complexes are stable (these priming complexes may only extend over 5 to 6 basepairs which corresponds to the length of the random sequence at the 3' end of primer A).

Template requirements for SIA

The SIA reaction has been successful in amplifying DNA from as few as 4 small marker chromosomes (the size of band 5q31). Thus the sensitivity lies in the range of 50 to 100 femtograms of DNA. The template DNA does not have to be purified or treated with proteinase K to remove the proteins. Since the reaction will work with minute amounts of DNA, contaminants that may inhibit enzyme reactions can be diluted out.

Procedure

Figure 3A:
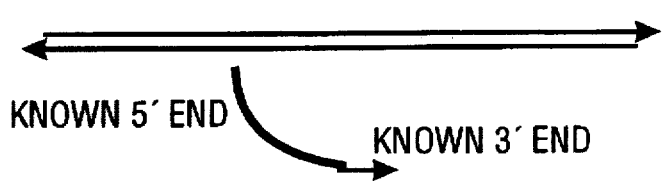
FIG. 3A is a representation of the double stranded DNA and the primer A with a known, or defined 5' end and a random 3' end.
Figure 3B:
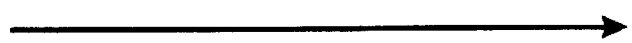
FIG. 3B is a representation of a single strand of the denatured DNA.
Figure 3C:
FIG. 3C is a representation of the annealing of the random portion of primer A with the single strand of DNA.
Figure 3D:
FIG. 3D is a representation of synthesis of the complementary strand of DNA by the DNA polymerase which is capable of primer displacement.

After the initial denaturation (FIG. 3B) of the DNA, primer A is annealed to the denatured, single stranded DNA (FIG. 3C). Because the primer has a random 3' end, it will anneal at random intervals to both strands of the original DNA. The 5 or 6 base pair hybrid between the primer and the original DNA is only stable at low temperatures, thus necessitating the low temperature initial polymerization reactions. These randomly annealed primers form the starting points for the first round of DNA synthesis (FIG. 3D).

Figure 3E:
FIG. 3E is a representation of the products of the first replication reaction.

The products of this first round of DNA synthesis are stretches of DNA that incorporate at their 5' ends the defined nucleotide sequence of primer A and contain up to several hundred base pairs of newly synthesized DNA that is complementary to the original source DNA (FIG. 3E). The DNA is denatured again and subjected to the same procedure as in round one. This time, however, the primers will also anneal at random intervals to the newly synthesized products of the first round and synthesis will be initiated from these priming sites (FIG. 3F and FIG. 3G). The products of this process will again contain at their 5' ends the defined sequence of primer A, then a large, newly synthesized stretch of DNA that is derived from the source DNA and finally at their 3' ends, the sequence that is complementary to the defined sequence of primer A (FIG. 3H). These products are now suitable substrates for the PCR process. They are copies of the source DNA flanked by the defined primer sequences, i.e. 5' they contain the original primer sequence and at their 3' terminus the inverted complement of this sequence. Normal PCR can now be performed by using as a primer, primer B, the defined sequence of primer A (FIG. 3I). The results are amplified DNA fragments that range in size from about 200 to 1200 base pairs and an average length of about 500 bp. They appear as a smear on an ethidium bromide stained agarose gel indicating random length and hence, random, sequence independent amplification.

Special points in the protocol

One of the primary advantages of this method is that the SIA is carried out in one reaction tube. Thus, no intermediate purifications are required (see Grothues et al., 1983).

The SIA reaction may be carried out in two different volumes. In the initial rounds, 4 to 6 µl volumes are used with the T7 DNA polymerase and primer A. The volume increases with every round as fresh T7 DNA polymerase is added (the enzyme is destroyed by the high temperature necessary for denaturation). The PCR cycles are preferably done in ten times the volume of the last T7 round. This increase in volume serves two purposes: First, it is an easy way to establish the buffer conditions that are optimal for Taq DNA polymerase (these are different from the optimal conditions of T7 DNA polymerase); Second, this increase in volume dilutes out primer A, which could act as a competitive inhibitor of the annealing of primer B to the ends of the DNA fragments.

Another mechanism to prevent this competitive inhibition is the design of a primer B, which extends for 5 to 8 bases further 5' than the defined part of primer A. As shown in FIG. 2A, FIG. 2B, FIG. 2C, FIG. 2D, FIG. 2E, and FIG. 2F, the part of primer B that is identical to primer A will hybridize in the first low stringency rounds (2 to 5 rounds) of the PCR reaction. These first rounds are enough to add the additional 5 to 8 bases of primer B to the sequence of the DNA fragments. In the high stringency rounds all of primer B is required to anneal and prime. The shorter primer A does not hybridize as efficiently under the higher stringency conditions. This reduces the competitive inhibition of primer A in the PCR reaction still further.

A major problem in some PCR reactions is the formation of primer dimers, i.e. the primers anneal to each other and form double stranded DNA pieces of about twice the primer length. Primer dimer formation can severely reduce the overall efficiency of the PCR reactions, because most of the dNTPs and primers will be incorporated into the primer dimers. The design of the SIA effectively reduces primer dimer formation. Since only one primer is used, each DNA fragment is flanked by an inverted repeat. After denaturation the single stranded fragments can form hairpin structures by using the inverted repeat to base pair one end with the other. Short, single stranded fragments will form these hairpin structures more readily because the ends are closer together than in longer fragments. Once a hairpin structure has formed primer B will no longer be able to anneal to the ends of the fragment since they have already annealed to each other to form the hairpin structure. Primer dimers are very short so they will form these hairpin structures faster than the amplified products, with the result that primer dimers will be amplified inefficiently.

This phenomenon, i.e. the hairpin structure formation, can also be used to control the average length of the fragments that are going to be amplified by varying the primer concentration. The higher the concentration of primer B, the shorter the average length of the amplified fragments will be; the lower the concentration the longer the average length of the amplified fragments.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

A preferred embodiment of the present invention is the fluorescence in situ hybridization analysis of chromosomes. In this method, an amplified DNA sample is labeled with a fluorescent marker and hybridized to a chromosomal preparation in order to determine the origin and copy number of the DNA in the sample. This is an excellent method to map chromosomes and to detect chromosomal deletions and rearrangements. The use of sequence independent amplification in conjunction with FISH greatly increases the speed and efficiency of analysis of microdissected chromosomes. For example, the time required to set up the reaction is less than an hour, and the results of the FISH analysis can be available within two days.

FISH Analysis of microdissected DNA

Figure 4A:
FIG. 4A shows two chromosomes 6 before dissection of the terminal portion of the long arm.
Figure 4B:
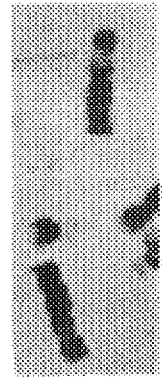
FIG. 4B shows two chromosomes 6 after dissection of the terminal portion of the long arm, indicated by the arrows.

Seventeen chromosomal segments containing bands 6q25-qter were microdissected from trypsin-Giemsa banded metaphase chromosomes, derived from Phytohemagglutinin (PHA) stimulated peripheral blood lymphocytes (FIG. 4A and FIG. 4B). The microdissection was performed on the stage of an inverted microscope using fine glass needles that were moved with an electronic micromanipulator (Eppendorf model 5170). The tips of the needles with the microdissected chromosomal material were broken off in a 0.5 ml Eppendorf reaction tube and overlaid with 5 µl of buffer A (40 mM Tris HCl (pH 7.5), 10 mM $MgCl_2$, 50 mM NaCl, 5 mM dithiothreitol, 50 µg/ml bovine serum albumin, 300 µM each dNTP, 3 µM Primer A, 5'-TGGTAGCTCTTGATCANNNNN-3', SEQ ID NO:1, FIG. 1).

Figure 2A:
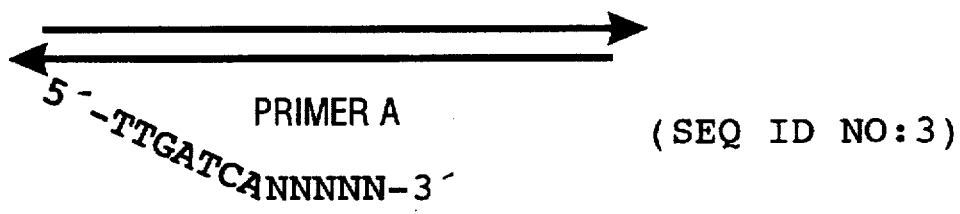
In FIG. 2A, FIG. 2B, FIG. 2C, and FIG. 2D, Primer A is a truncated representation of the full sequence of the actual primer A (SEQ ID NO:1) used in the development of the present invention. The primer A in FIG. 2A, FIG. 2B, FIG.
Figure 2B:
Figure 2C:
Figure 2D:
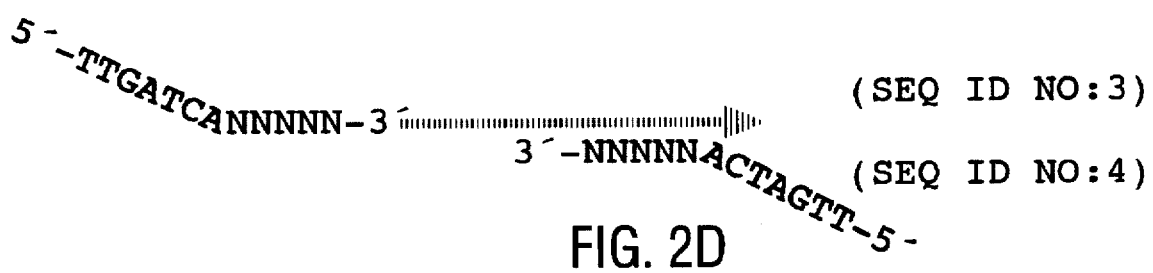

Primer A, SEQ ID NO:1, has a five nucleotide random 3' segment and a sixteen nucleotide 5' portion of defined sequence. The underlined part of the primer represents a BclI restriction enzyme site. The DNA was denatured by a 2 minute incubation at 97° C. and cooled to 4° C. to let the primer anneal at random sites (FIG. 2B). One unit of T7 DNA polymerase (USB: Sequenase version 2.0) was added in 2.5 µl of buffer A and the temperature was ramped to 37° C. over an 8 minute interval and kept at 37° C. for 8 minutes resulting in the synthesis of the first strand of DNA (FIG. 2C).

Figure 2E:
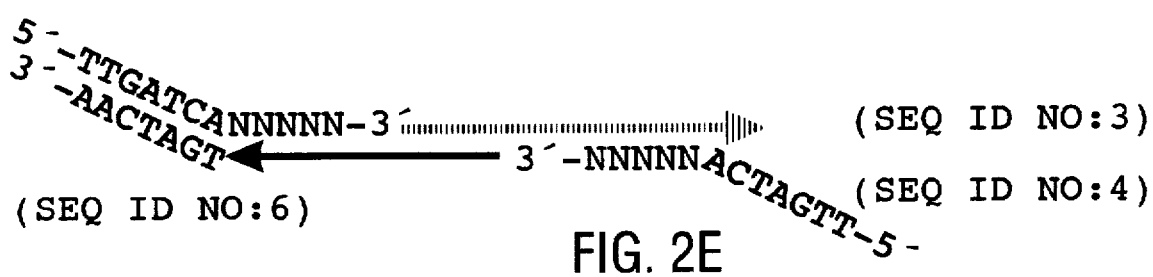
FIG. 2E represents the replication of the product from step 2C by DNA polymerase.
Figure 2F:
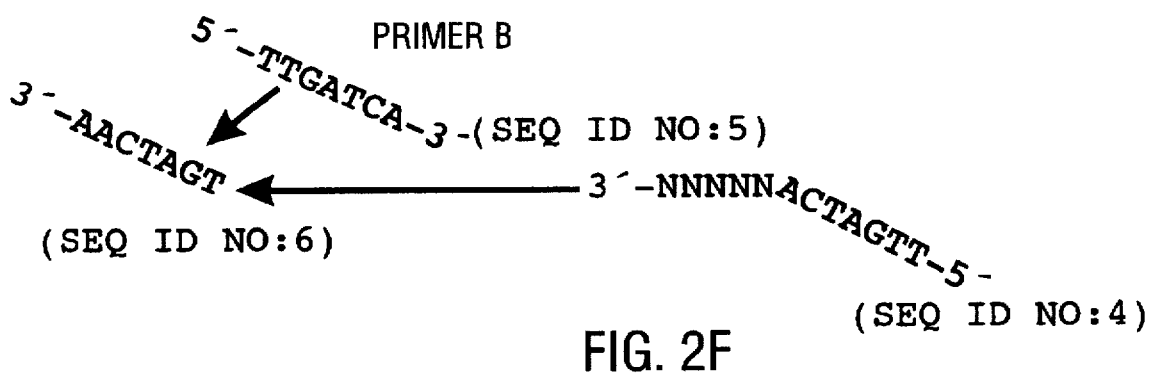
FIG. 2F represents the PCR amplification of the DNA products of the initial reactions. In this PCR amplification, the reaction is primed by primer B.

T7 DNA polymerase was chosen for this step because it functions well at the low temperatures at which the random priming complexes are stable and because it possesses strand displacement synthesis capabilities. Strand displacement synthesis enables the enzyme to synthesize long stretches of DNA by displacing other primers that have already annealed to the DNA. After denaturation and annealing (FIG. 2D), the synthesis step with T7 DNA polymerase was repeated one more time by adding fresh enzyme in 2.5 µl of buffer A (FIG. 2E). In this second synthesis step, primer A, SEQ ID NO:1, will also prime on the products from the first round (as shown in FIG. 2I). The products of this second synthesis step were now suitable for PCR amplification; an unknown stretch of genomic DNA is flanked 5' by the known sequence of the primer and 3' by the inverted complement of this sequence (FIG. 2E).

PCR was carried out by adding 90 µl of buffer B (6.6 mM Tris HCl (pH 9.0), 0.25 mM $MgCl_2$, 55 mM KCl, 0.01% W/V gelatin, 77 µM each dNTP, 2.2 µM Primer B (5'-AGAGTTGGTAGCTCTTGATC-3'), seq id no:2, 2.5 U Taq DNA polymerase). The underlined part of the primer B sequence, seq id no:2, is identical to the 15 5' nucleotides of primer A, SEQ ID NO:1. Five low stringency cycles with denaturation at 94° C. for 50 seconds, annealing at 42° C. for 5 minutes, a ramp to 72° C. for 6 minutes and synthesis at 72° C. for 3 minutes were followed by 33 PCR cycles with denaturation at 94° C. for 50 seconds, annealing at 56° C. for 1 minute and synthesis at 72° C. for 2 minutes. The products of the SIA ranged in size from 200 to more than 800 bp. To judge the background amplification and the quality of the amplification, two negative and one positive control reaction were performed with each amplification.

One 1 µl aliquot of the amplified product was biotin-labeled with Bio-11-dUTP (Enzo Diagnostics) in a PCR reaction under the following conditions: 1.5 mM $MgCl_2$, 50 mM KCl, 10 mM Tris HCl (pH 8.3), 0.01% W/V gelatin, 100 µM each dATP, dGTP, and dCTP, 75 µM dTTP, 100 µM Bio-11-dUTP, 2 µM Primer B and 2.5 U/µl Taq DNA polymerase. 18 cycles of 50 seconds at 94° C., 1 minute at 56° C. and 3 minutes at 72° C. were performed. The labeled products were treated with DNAse I (83 pg/µl) for 30 min at room temperature before they were used for FISH.

The amplified products were used to construct chromosome band-specific fluorescence in situ hybridization painting probes. The SIA products were labeled with biotin, Spectrum Orange (Imagenetics) or Spectrum Green (Imagenetics). The products were also used to construct chromosome band-specific recombinant DNA libraries in plasmid vectors with inserts ranging in size from 200 to 1000 bp. The chromosomal origin of some of these clones could be confirmed. Also, some of these clones were sequenced and PCR primer pairs derived from these sequences resulted in amplification of specific products from human genomic DNA. One of these primer pairs was also used to screen successfully a mega insert YAC library.

Figure 4C:
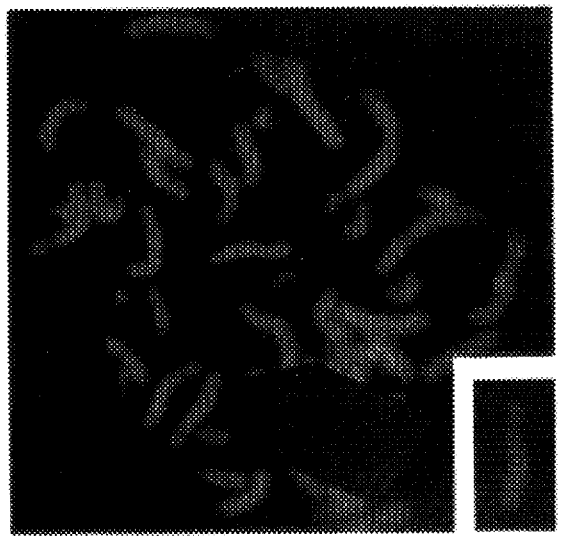
FIG. 4C is a DAPI stained metaphase cell and partial metaphase cell (inset). The chromosome 6 homologues are identified by arrows.
Figure 4D:
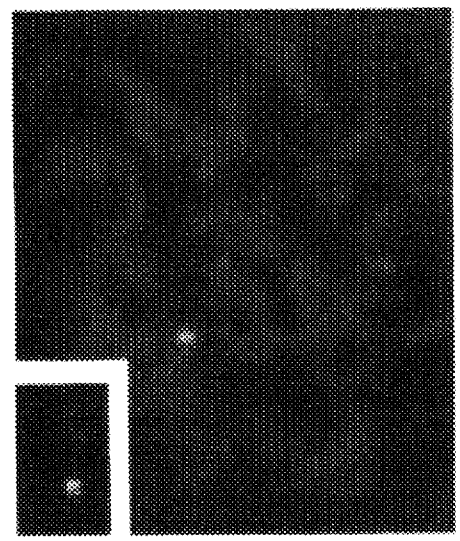
FIG. 4D is the same chromosomes after FISH with the biotinylated amplification products from seventeen 6q25-qter segments showing specific hybridization to 6q25-qter. Only the signal of the chromosome 6 in the inset was amplified with goat anti-avidin conjugated with FITC.
Figure 5A:
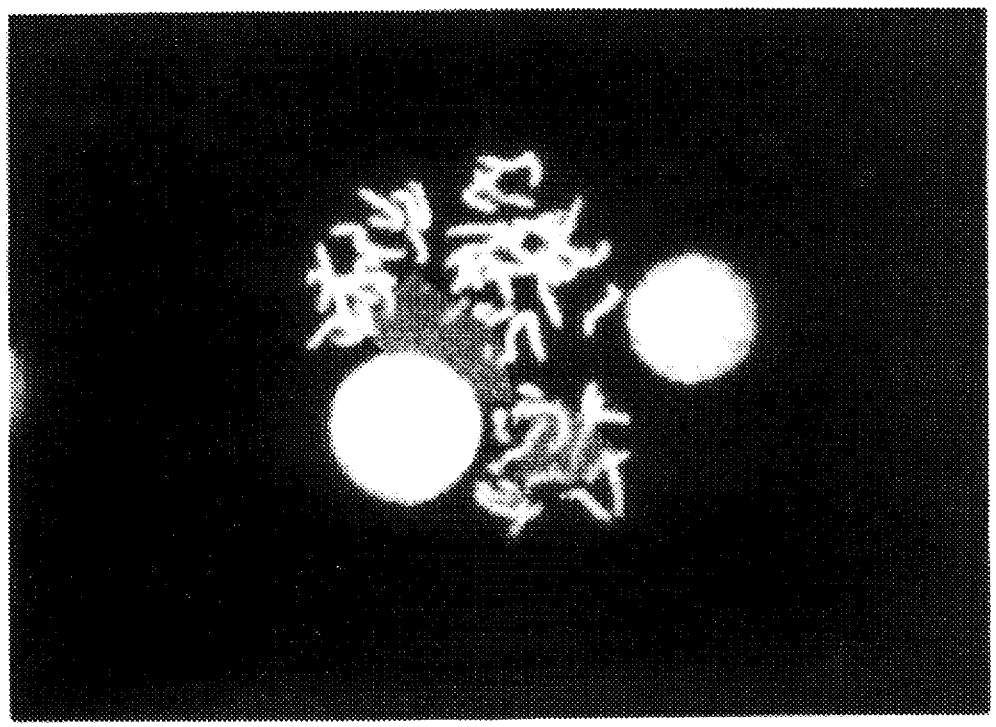
FIG. 5A represents DAPI stained metaphase and interphase cells following hybridization of the YAC Not-42 probe. Arrows point to the two chromosome 21 homologues.
Figure 5B:
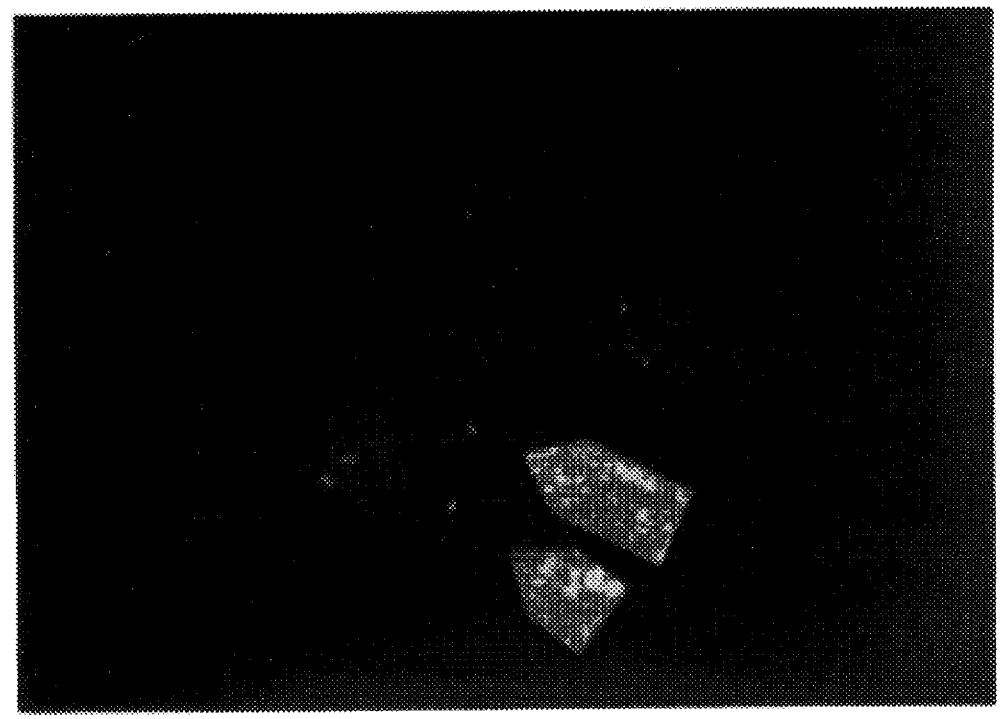
FIG. 5B represents a biotin labeled YAC Not-42 (420 kb) probe which was detected with FITC; the signal was not amplified.

FISH of the biotinylated products was performed as described previously (Rowley et al., 1990). Metaphase chromosomes were identified by DAPI staining (4',6-diamidino-2-phenylindole dihydrochloride) (FIG. 4C). The hybridization signal of the probes was detected by fluorescein-isothiocyanate (FITC)-conjugated-avidin and amplified (only in inset FIG. 4D) with goat anti-avidin conjugated with FITC (Vector Laboratories). A strong signal covering bands 6q25-qter can be seen on all three chromosome 6 homologues in FIG. 4D thus demonstrating the specificity and efficiency of the SIA method.

EXAMPLE II

Yeast artificial chromosomes (YACs) are ideal vectors for the detailed mapping of large stretches of DNA (Burke et al., 1987). One of the main disadvantages of the previous YAC cloning systems was that there were no methods available to purify the YAC DNA in large quantities. High molecular weight DNA can be prepared from yeast clones carrying YACs and the YACs can be isolated on a pulsed field gel. This approach, however, yields only very small amounts of pure YAC DNA. This is a major disadvantage because many important uses of these large inserts, e.g. screening cDNA libraries or fluorescence in situ hybridization (FISH) analysis, would require larger amounts of purified YAC DNA.

The method of the present invention uses a different strategy to amplify the YAC DNA after its isolation in a pulsed field gel (Bohlander et al., 1991, 1992). This sequence independent amplification (SIA) method requires no prior purification of the DNA, and no restriction enzyme digestion or ligation. It also has no a priori sequence requirements for the DNA that is to be amplified, unlike the linker-adapter method which requires certain restriction sites to be present. This results in a substantial improvement in the speed of probe preparation and in the quality of the FISH signal over earlier strategies.

FISH Analysis of YAC DNA

In an example of this method, several different YACs of sizes ranging from 100 kb to 420 kb were isolated in 1% low melting agarose (SeaKem GTG, FMC) by pulsed field gel electrophoresis. YAC Not-42 (420 kb) (Gao et al., 1991), YAC 88E10 (330 kb), and YAC C3G4 (100 kb) (Burke et al., 1987) were used. YAC Not-42 maps to chromosome band 21q22, and both YAC A88E10 and C3G4 map to 9p21. DNA bands corresponding to the YACs were excised from the gel and were transferred to Eppendorf tubes. TE buffer (10 mM Tris-HCl pH 7.9, 1 mM EDTA) was added equal to three times the volume of the agarose slice, the tubes were incubated at 65° C. for 5 min, and the contents mixed thoroughly.

The sequence independent amplification was carried out as described in Example I with some modifications. For example, 0.5 µl of the diluted YAC DNA was added to 4 µl of buffer A (40 mM Tris HCl (pH 7.5), 10 mM $MgCl_2$, 50 mM NaCl, 5 mM dithiothreitol, 50 µg/ml bovine serum albumin, 300 µM each dNTP), and 1.25 µM Primer A, 5'-TGGTAGCTCTTGATCANNNNN-3' (SEQ ID NO:1). The DNA was denatured at 94° C. for 2 minutes and cooled to 13° C. to allow primer A, SEQ ID NO:1, to anneal at random sites. Next, 0.5 units of T7 DNA polymerase (USB: Sequenase version 2.0) were added in 0.5 µl of buffer A and the temperature was gradually increased from 13° C. to 37° C. over a 3 minute interval and kept at 37° C. for 2 minutes. After denaturation and annealing, this synthesis step was repeated three times by adding fresh T7 enzyme in 0.5 µl of buffer A each time. The polymerase chain reaction (PCR) was carried out by adding 90 µl of buffer B (6.6 mM Tris HCl, pH 9.0, 55 mM KCl, 0.01% (w/v) gelatin, 77 µM each dNTP, 1.4 µM Primer B, 5'-AGAGTTGGTAGCTCTTGATC-3' (SEQ ID NO:2), and 2.5 U Taq DNA polymerase). The underlined part of primer B, SEQ ID NO:2 is identical to the 15 nucleotides of the 5' end of primer A, SEQ ID NO:1. Five low stringency cycles with denaturation at 94° C. for 45 seconds, annealing at 44° C. for 2 minutes, a 2 minute ramp to 72° C. and synthesis at 72° C. for 2 minutes were followed by 30 PCR cycles with denaturation at 94° C. for 45 seconds, annealing at 56° C. for 45 seconds and synthesis at 72° C. for 2 minutes. The amplified products ranged in size from 300 to 1000 bp. These products were then labeled with biotin or Spectrum-Orange as described in detail in Example IV, infra.

FISH was performed as described previously (Rowley et al., 1990). Metaphase chromosomes were identified by DAPI staining (4',6-diamidino-2-phenylindole dihydrochloride). The hybridization signals of the biotin labeled probes were detected by fluorescein-isothiocyanate (FITC) conjugated avidin (Vector Laboratories). The Spectrum-Orange labeled probes could be visualized directly by fluorescence microscopy.

FIG. 4A and FIG. 4B show metaphase and interphase cells hybridized with YAC Not-42, which was labeled with biotin and detected with FITC-conjugated-avidin. A very strong signal was observed on both chromosome 21 homologues. There were also two distinct signals in each of the interphase nuclei. Both YAC A88E10 labeled with Spectrum Orange (FIG. 4C), and YAC C3G4 labeled with biotin and detected with FITC conjugated avidin (FIG. 4D), gave strong signals in the middle of the short arm of both chromosome 9 homologues and gave two distinct signals in the interphase nuclei. The FISH signal intensities achieved with this method, even for small YACs, is so strong that it allows the easy detection of the signal without a CCD camera system or other image enhancing methods.

This method has been used for the analysis of 13 different YACs, ranging in size from 100,000 to greater than 2 million base pairs. In each case, strong signals were observed in metaphase and interphase cells, suggesting that the method can be used readily with YACs of varying sizes. The following number of signals were observed in interphase nuclei for YAC Not-42. In 1000 nuclei scored, 3.3% showed one signal, 97.1% showed two signals, 0.7% showed three signals and 0.2% showed four signals. These results are comparable to those observed in the inventors' laboratory with centromere specific probes.

EXAMPLE III

The following is a detailed protocol for SIA of YAC DNA isolated from pulsed field gels. The method is also applicable to microdissected chromosomes, DNA contained in any number of vectors such as plasmids, viral vectors, Lambda phage, cosmids, or even DNA samples from whole cells, mitochondria, chloroplasts or from any other source. Certain modifications may have to be made to specific steps in the method in order to achieve the best results with DNA from various sources. However, these modifications are well known to those who practice the art and the best conditions can be found without undue experimentation.

Detailed Laboratory Protocol for SIA

Methods

1. Reaction tubes to be used in the reaction are placed in the Stratalinker and irradiated for ten minutes with UV light.
2. The laminar flow hood is allowed to run for at least five minutes. The inside of the hood and the tube racks to be used are wiped with 70% ETOH.
3. The following mixtures are prepared:

| Tube A (6.0 µl final volume per sample) |
| --- |
| 0.6 µl 10X MAP buffer |
| 0.3 µl 1 mg/ml BSA |
| 0.6 µl 3 mM each dNTP |
| 5.0 µl $d_2H_2O$ |

| Tube B (54 µl final volume per sample) |
| --- |
| 5.4 µl 10X BP buffer |
| 2.4 µl 3 mM each dNTP |
| 47. µl $d_2H_2O$ |

4. Tubes A and B are irradiated for 10 minutes in the Stratalinker. The tubes must be open while exposing to UV and then closed immediately after exposure is complete, starting with tube A. Next the tubes are returned to the hood.
5. Primer A is added to tube A. For each 6.0 µl total, 0.375 µl of 20 µM Primer A is added for a final concentration of 1.25 µM.

Primer A Sequence

5'-TGGTAGCTCTTGATCANNNNN-3' (SEQ ID NO:1)

After addition of the primer, the reaction is mixed by pipetting carefully.

6. Primer B is added to tube B. For each 54 μl total, 3.75 μl of 20 μM Primer B is added for a final concentration of 1.25 μM.

Primer B Sequence

5'-AGAGTTGGTAGCTCTTGATC-3' (SEQ ID NO:2)

7. Small reaction tubes are labeled for each template while tubes A and B are irradiating including tubes for a positive and a negative control.
8. Into each tube is aliquoted 4 μl of buffer A with Primers. Afterwards the tubes are placed on ice.
9. To the remaining buffer in tube A, 0.14 μl of T7 DNA Polymerase ([13 U/μl] USB Sequenase Ver 2.0), is added per sample, and placed on ice.
10. Into tube B 0.4 μl of Taq Polymerase [5 U/μl], is added per sample, and placed on ice.
11. The reactions are then moved to the Template Tamer which has previously been exposed to UV irradiation for approximately 10–15 minutes.
12. No template is added to the negative control tube. In the sample tubes the appropriate template is added depending on the origin of the template DNA: for Cosmid and Phage DNA, 0.5 μl of template diluted to 0.1–1 ng/μl in TE is used, for YACS, 0.5 μl of the low melt slice is used (diluted to 0.25% low melting point agarose concentration with TE. Alternatively, if regular agarose is used, boil for 5 min, or for the microdissection buffer A is added to the tube with the microdissected fragments. Into the positive control tube 0.5 μl of Placental DNA [20 pg/μl] is added).
13. All reaction tubes should be placed in the thermocycler and denatured at 97° C. for 2 minutes. During the denaturing step, tubes A and B are vortexed briefly and spun down.
14. The reaction tubes are removed from the thermocycler and placed on ice in the Template Tamer. 0.5 μl of buffer A is added with T7 Polymerase, being careful to draw up the correct amount. The tubes are spun down and placed in the thermocycler. The reactions are then run according to the following parameters:
Step 1: 13° C., hold for 1:00
Step 2: Ramp for 3:00 to 37° C., hold for 2:00
Step 3: 94° C., hold for 0:50 Cycles 1×
Step 4: Soak: 4° C.
15. The tubes are then removed from the thermocycler and returned to the Template Tamer. An additional 0.5 ul of A is added and the tubes are spun down. The reaction is repeated as above. This procedure is repeated two more times for a total of 4 cycles with T7 DNA Polymerase.
16. After the fourth cycle of incorporation with T7 Polymerase, 54 ul of buffer B with Taq Polymerase is added. The tubes are spun down and the reactions are run according to the following parameters:
Step 1: 94° C., hold for 2:00
Step 2: 94° C., hold for 0:45
Step 3: 44° C., hold for 3:00
Step 4: Ramp for 2:00 to 72° C., hold for 2:00 Cycle from Step 2, 5×
Step 5: 94° C., hold for 0:45
Step 6: 56° C., hold for 0:45
Step 7: 72° C., hold for 2:00 Cycle from Step 5, 30×
Step 8: 72° C., hold for 7:00
Step 9: Soak, 4° C.
17. This PCR run takes approximately three hours to complete.
18. Next the PCR products are run on a 1.5% minigel to determine their size range. They should be between 200 and 400 kb. 10 ul of the PCR product plus 2 μl of loading dye is added to each lane of the gel. The gel is run at 45 volts for two hours, stained with EtBr and observed under UV light. The negative control should be blank, with the positive control and samples being smears in the proper size range. As a size standard, 1.0 μl of 123 BP marker is used, diluted up to 10 μl with TE.

| Buffers |
| --- |
| 10X MAP buffer |
| 400 mM Tris HCl pH 7.5 |
| 100 mM MgCl₂ |
| 500 mM NaCl |
| 50 mM DTT |
| 10X BP buffer |
| 66 mM Tris HCl pH 9.0 |
| 550 mM KCl |
| 0.11 % (w/v) Gelatin |

The SIA products from the isolated YACs were labeled as described in Example IV and used for FISH experiments. The resulting signals on metaphase cells as well as on interphase cells were superior in quality to any YAC FISH signals obtained with other methods (i.e. with ALU-PCR or with nick-translation of total yeast DNA) in the inventors' laboratory. The signal intensity and consistency in interphase cells was also better than with either cosmid or lambda phage probes.

Small recombinant DNA libraries from YACs were constructed from the products of the SIA. The SIA products from the YAC can also be used to select for transcribed sequences (see Example X, infra).

EXAMPLE IV

The following example is a detailed protocol for the labeling of SIA products. The SIA products may be labeled in two different ways. They may be labeled with biotin in a second PCR by incorporation of Bio-11-dUTP under the following conditions: 1.5 mM MgCl₂, 50 mM KCl, 10 mM Tris HCl (pH 8.3), 0.01% (w/v) gelatin, 150 μM each dATP, dGTP, and dCTP, 110 μM dTTP, 40 μM Bio-11-dUTP, 1.5 μM Primer B and 1 U/30 μl Taq DNA polymerase. Preferably about 18 PCR cycles may be run with about 50 seconds at about 94° C., about 1 minute at about 56° C. and about 2 minutes at about 72° C. 1 μl of the sequence-independent amplification products may be used as template and the reactions may be performed in 30 μl volumes.

Products may also be labeled with the fluorophore Spectrum-Orange (Imagenetics, Naperville, Ill.) by performing a PCR under the same conditions as above with each dNTP at 150 μM and the Spectrum-Orange-dUTP at 30 μM. The labeled PCR products (either with Biotin or with Spectrum-Orange) may then be treated with DNase I (at a DNase I concentration of 200 pg/μl) for 10 to 20 min at room temperature. The DNase I is inactivated at 65° C. for 10 minutes.

Labeling of SIA Products

Methods

1. Preparation of the Biotinylation Master Mix, allowing 30 µl for each product to be labeled.

| Biotinylation Master Mix (volumes per sample) |
| --- |
| 3.0 µl 10X Taq PCR Buffer (1.5 mM MgCl$_2$ final) |
| 4.5 µl dNTP-dTTP (1 mM) final 150 mM |
| 3.3 µl dTTP (1 mM) final 110 mM |
| 4.0 µl bio-11-dUTP (0.3 mM, Enzo) final 40 mM |
| 0.2 µl Taq Polymerase (5 U/µl) |
| 1.875 µl Primer B (20 µM) final 1.25 µM |
| X µl d$_2$H$_2$O make total volume of mix 29 µl |

A 10× master mix for the dNTPs can also be made with all dNTPs present at 1.5 mM except for dTTP which will be at 1.1 mM.

2. 1 µl of primary PCR product is added to 29 µl of the Biotinylation Master Mix. The PCR reactions are run according to the following temperature profiles in a Perkin Elmer 9600 with thin-walled micro tubes, for example.
   Step 1: 94° C., 2:00 minutes
   Step 2: 94° C., 30 seconds
   Step 3: 56° C., 30 seconds
   Step 4: 72° C., 2:00 minutes
   Run the Cycle from step 2, 22 times
   Step 5: 72° C., 7:00 minutes
   Soak at 4° C.

3. Next a 1.5% minigel is prepared to run the PCR products before and after DNase treatment.

4. 27 µl is removed from the PCR tube and placed in a 1.5 ml microfuge tube. The remaining 3 µl of product will be used as the pre-DNase sample.

5. The DNase is diluted, using the 10× Adjusting Buffer, to 1:2000 (the dilution has to be empirically determined).

6. 3 µl of the dilute DNase is added to each sample tube. The DNase is placed in the cap of the tube and then spun in the microfuge. The tube is then incubated at room temperature for 10 minutes.

7. After 10 minutes the reaction is stopped by incubating for 10 minutes at 65° C.

8. 3 µl is removed for the post-DNase sample. The rest is placed at –20° C.

9. The before and after samples are run on a 1.5% gel at 40 V for two hours.

10. The concentration and extent of DNase digestion is estimated. The smear on the digested lanes should move down visibly and the fragment size should range between 100 and 300 bp.

10× DNase Adjusting Buffer
0.5M Tris HCl pH 7.5
5 mM MgCl$_3$
DNase Stock Solution
Final Concentration:
50% Glycerol
20 mM Tris HCl pH 7.5
1 mM MgCl$_2$

| DNase Buffer Solution: |
| --- |
| 2.0 ml 1M Tris HCl pH 7.5 |
| 0.1 ml 1M MgCl$_2$ |
| 97.9 ml d$_2$H$_2$O |

One may use, for example DNase BM cat.#104-132, 20,000 U. 5.08 mg, 0.5 ml of DNase buffer is added to the lyophilized DNase to reconstitute. Then 0.5 ml of glycerol is added. The DNase is then mixed gently, but not vortexed. It can be stored at –20° C. for up to one year.

EXAMPLE V

Another embodiment of the present invention is the amplification of cosmid inserted DNA. Cosmids are plasmid derived vectors that also contain the cos sequences that allow the DNA to be packaged into a lambda phage in vivo. It is frequently difficult to purify cosmid DNA in adequate quantities or to a sufficient purity to allow traditional nick translation reaction. A common problem is laboratories experienced in FISH analysis receive DNA probes sent from outside investigators for mapping. The quality of DNA received varies widely. The problem is overcome by using the SIA amplification of the DNA and subsequent labelling according to the disclosed methods. The method is reliable and provides good FISH results.

Amplification of Cosmid DNA

Picogram amounts of cosmid DNA (linearized and supercoiled template) were amplified by the SIA method and then labeled in the same fashion as described above. The FISH signal quality obtained with these probes was the same as the quality obtained from the same cosmids after labelling with nick translation using microgram amounts of DNA. A cosmid from the ABL gene amplified with SIA and PCR labeled was employed to verify complex rearrangements. FIG. 6A and FIG. 6B shows FISH signals from 100 pg to 1 ng of cosmid DNA amplified by SIA. FIG. 6A was from chromosome 21 and FIG. 6B mapped from chromosome 5 band q31.

EXAMPLE VI

Lambda phage clones (picogram amounts) were amplified with the SIA method (the human insert was between 13 and 20 kilobase pairs in length) and labeled by the same method as described above. The signal intensity was again comparable to the signal intensity achieved after nick translation of the same phage clones. In some cases the conventional nick translation labeling method did not give any FISH signals whereas the SIA method resulted in good signals at the first try. These results indicate that SIA is able to amplify even DNAs of low complexity (such as phage DNA).

Amplification of Phage DNA

FIG. 7 represents a typical FISH signal obtained from amplification of 100 pg to 1 ng of total phage DNA. The human insert of the phage was approximately 15 kbp. Clear signals are observed on both homologues of chromosome 5 band q31.

EXAMPLE VII

In a prophetic example, the method of the present invention can also be applied to amplifying into unknown sequences from one known sequence. This concept could also be called half-sided sequence independent amplification.

One Sided PCR

In this approach, the first round of replication of the denatured template is accomplished at low temperatures by a primer that has a random 3' end and a defined 5' end (just like primer A) and a DNA polymerase that works well at low temperatures and has no strand-displacement activity (such as DNA Pol III). After denaturation, the second round of amplification is done with a specific primer for the sequence of interest at annealing temperatures that are high enough to exclude nonspecific annealing by the first or the second primer. To prevent the formation of excessive mounts of primer dimers and of very short products it is necessary to make the defined sequence of the first primer identical to the sequence of the second primer.

The one-sided approach is especially valuable to obtain sequences that are at the ends of YAC or cosmid inserts (the known sequence would be the vector arms). The method could also be used to obtain sequences from the other side of chromosomal translocations or the unknown part of fusion transcripts.

The use of a nested primer for the defined sequence would enhance the specificity of this technique. Preliminary experiments have shown that great care must be taken in the choice of the appropriate DNA polymerase for this scheme. The inventor has noted that the choice of polymerase in the one sided PCR method makes a significant difference in the specificity of the one sided PCR reaction. The use of T7 polymerase in the first random step results in unspecific amplification of the DNA even when the specific one sided DNA target is not within the template. This result can be explained by the strand-displacement capabilities of T7. When Klenow Fragment was used as the DNA polymerase for the first round, this unspecific amplification was greatly reduced. It is contemplated that optimization may be obtained by the choice of the DNA Polymerase in combination with variations in the template and primer concentration and also the use of nested primers as mentioned.

EXAMPLE VIII

In another prophetic example, the method of the present invention can be used to achieve preferential amplification adjacent to microsatellite repeats or other interesting sequences. A modification of the one sided approach is to use a defined sequence for the two primers that is specific for a microsatellite repeat or any other interesting sequence such as the trinucleotide repeat sequences found in certain important genes.

Preferential Amplification Adjacent to Sequences of Interest

An example of this embodiment would be the amplification of sequences adjacent to microsatellite repeats. It is contemplated that the defined sequence immediately 5' to the random part of the first primer is modified to CACACACA. Then a one sided PCR protocol is performed using only one very low stringency cycle with a DNA polymerase that does not have strand displacement capabilities. After dilution, PCR is performed, e.g. with a "hot start" technique, with the corresponding primer which lacks the 3' random sequence. This is analogous to the SIA protocol.

EXAMPLE IX

In another prophetic example of sequence independent amplification, this method can be used to compare two DNA sources to obtain conserved sequences. When complex DNA mixtures of different origins are compared by hybridization to find common sequences the DNA from one source (the driver) will be in great excess whereas the DNA from the other source (the tester) will have a very low concentration. The portion of the tester that anneals to the driver will have to be amplified after the hybridization either to do further work with it or to do another round of selection by hybridization. In most instances, the sequence composition of the tester is not known, and especially the sequences of the tester that are in common with the driver. SIA is a convenient method to make all of the tester DNA PCR amplifiable by a very simple procedure.

For example, the procedure may be used to determine which sequences, if any, in a cosmid with a human genomic insert are conserved between man and mouse. One would perform the following:

(1) Perform SIA on the cosmid DNA (2) Hybridize amplified sequences from the cosmid to whole mouse DNA immobilized on a filter or on magnetic beads (3) Wash with appropriate stringency so that only DNA from the cosmid with sequence homology to the mouse is still hybridized to mouse DNA (4) Elute desired DNA from mouse DNA by boiling or other means of denaturation (5) Amplify DNA eluted from mouse DNA, then clone and analyze Alternatively, the tester DNA (i.e. the cosmid) may be obtained by microdissection of chromosomal fragments, phage lambda insert DNA, YAC DNA or total genomic DNA.

EXAMPLE X

Another prophetic embodiment of sequence independent amplification is the selection of transcribed sequences. After a YAC has been excised from a pulsed-field gel and amplified by the SIA method, as in Example I, supra, the products can be used to select for transcribed sequences. The selection is done by hybridization of the SIA products against a cDNA library (the hybridization can take place in liquid or with the cDNA immobilized on a solid support such as a nitrocellulose filter or on magnetic beads). After a washing step which removes the unhybridized DNA, the fragments from the SIA reaction that hybridized specifically to the cDNA are eluted by, for example, a higher temperature wash and amplified by PCR. This procedure can be repeated to obtain a higher enrichment for the selected sequences in the SIA products. The source of DNA may be a cosmid, phage insert (or total phage), microdissected chromosome fragment (or whole chromosome) or any other small quantity of DNA source.

EXAMPLE XI

Numerous additional applications of the disclosed methods are contemplated by the inventor. These examples are as follows:

Multilocus DNA typing by PCR from Single Cells

In certain circumstances it will be desirable to know the alleles of a great number of loci in the DNA from a single cell or a limited number of cells or DNA (e.g. in preimplantation diagnostics, polar body diagnostics, sperm or oocyte typing, forensic samples, the analysis of ancient DNA, etc.). PCR can be performed for a number of loci simultaneously; this is called multiplex PCR. However, the number of loci, i.e. the number of primer pairs, that can be used at the same time is limited. Usually no more than 5 or 6 loci are efficiently amplified together. The more primer pairs are used the more complex and unpredictable the interactions between these primers will become (perhaps leading to the formation of primer dimers or resulting in a great number of unspecifically amplified bands). To circumvent this problem, Zhang et al. (1992) have proposed a general amplification method for the whole genome. This method is called primer-extension preamplification (PEP). The limited DNA sample is first preamplified (PEP uses a mixture of random 15 base oligonucleotides and Taq polymerase, and fifty cycling rounds), then the sample is divided and used as template for the different PCR reaction. The PEP procedure results in linear amplification of the target DNA. In contrast, the disclosed SIA results in exponential amplification of the target DNA. SIA should therefore be more efficient at amplifying small amounts of DNA and will yield more DNA for more different typing reactions than the PEP procedure.

Sequence-Independent RNA Amplification

The SIA method is readily adapted to perform sequence-independent amplification of RNA. This may be desired for example to analyze the RNA content of a single cell or from a small population of cells (e.g., from single cells or a small number of cells to generate cell type specific cDNA libraries). The first round employs primer A and a reverse transcriptase to produce the first cDNA strand. This strand has the defined primer sequence at its 5' end. Then one or several rounds, preferably 3, with T7 DNA polymerase and primer A follow. After that, a normal PCR is performed using primer B as primer. Kits are also envisioned which include the basic reagents from the SIA kit plus reverse transcriptase, RNase inhibitors and RNase free buffers (the buffer conditions for T7 DNA polymerase and some reverse transcriptases are identical, so that all of the first steps can be performed in the same buffer). RNA has been amplified using the SIA procedure.

Selection of DNa Sequences that are Targets for DNA Binding Proteins

To determine the target sequence for DNA binding proteins (e.g. transcription factors), a number of selection methods have been described in the literature. One uses a population of synthetic oligonucleotides with defined primer sequences at either end that are selected for binding to a certain protein. After each binding and washing step, the oligonucleotides that bound to the protein are eluted and amplified by PCR. This is repeated a number of times. Another approach is the use of genomic DNA instead of oligonucleotides for the selection step. This genomic DNA has been made PCR amplifiable by the linker ligation method previously described (Lüdecke et al., 1989). An obvious way to simplify this protocol is to use SIA to make the genomic DNA PCR amplifiable (with the advantages previously discussed).

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Baldini A, Ross M, Nizetic D, Vatcheva R, Lindsay E A, Lehrach H, Siniscalco M: Chromosomal assignment of human YAC clones by fluorescence in situ hybridization: Use of single-yeast-colony PCR and multiple labeling. Genomics 14: 181–184 (1992).

Bohlander S K, Rassool F V, Espinosa R, Le Beau M M, Rowley J D, Díaz M O: A method for the rapid sequence-independent amplification of microdissected chromosomal material. Am J Hum Genet Suppl 49: 365 (1991).

Bohlander S K, Espinosa R, Le Beau M M, Rowley J D, Díaz M O: A method for the rapid sequence-independent amplification of microdissected chromosomal material. Genomics 13: 1322–1324 (1992).

Breen M, Arveiler B, Murray I, Gosden J R, Porteous D J: YAC mapping by FISH using Alu-PCR-generated probes. Genomics 13: 726–730 (1992).

Burke D T, Carle G F, Olson M V: Cloning of large segments of exogenous DNA into yeast by means of artificial chromosome vectors. Science 236: 806–812 (1987).

Gao J, Erickson P, Gardiner K, Le Beau M M, Diaz M O, Patterson D, Rowley J D, Drabkin H A: Isolation of a yeast artificial chromosome spanning the 8;21 translocation breakpoint t(8;21)(q22;q22.3) in acute myelogenous leukemia. Proc Natl Acad Sci USA 88: 4882–4886 (1991).

Grothues D., Cantor, C. R., Smith C. L., PCR amplification of megabase DNA with tagged random primers (T-PCR), Nucleic Acids Research, 21 (5): 1321–1322, (1983).

Kao, F.-T., and Yu, J.-W.: Chromosome microdissection and cloning in human genome and genetic disease analysis. Proc. Natl. Acad. Sci. USA 88: 1844–1848 (1991).

Lengauer C, Green E D, Cremer T: Fluorescence in situ hybridization of YAC clones after Alu-PCR amplification. Genomics 13: 826–828 (1992).

Lüdecke, H.-J., Senger, G., Claussen, U., and Horsthemke, B.: Cloning defined regions of the human genome by microdissection of banded chromosomes and enzymatic amplification. Nature 338: 348–350 (1989).

Meltzer, P. S., Guan X.-Y., Burgess, A., and Trent, J. M.: Generation of region specific probes by chromosome microdissection: A novel approach to identify cryptic chromosomal rearrangements. Nature Genetics 1: 24–28 (1992).

Nelson D L, Ledbetter S A, Corbo L, Victoria M F, Ramirez-Solis R, Webster T D, Ledbetter D H, Caskey C T: Alu polymerase chain reaction: A method for rapid isolation of human-specific sequences from complex DNA sources. Proc Natl Acad Sci USA 86: 6686–6690 (1989).

Rowley J D, Díaz M O, Espinosa R, Patel Y D, van Melle E, Ziemin S, Taillon-Miller P, Lichter P, Evans G A, Kersey J H, Ward D C, Domer P H, Le Beau M M: Mapping chromosome band 11q23 in human acute leukemia with biotinylated probes: Identification of 11q23 translocation breakpoints with a yeast artificial chromosome. Proc Natl Acad Sci USA 87: 9358–9362 (1990).

Sutcliffe J S, Zhang F, Caskey C T, Nelson D L, Warren S T: PCR amplification and analysis of yeast artificial chromosomes. Genomics 13: 1303–1306 (1992).

Telenius, H., Pelmear, A. H., Tunnacliffe, A., Carter, N. P., Behmel, A., Ferguson-Smith, M. A., Nordenskjöld, M., Pfragner, R., and Ponder, B. A. J.: Cytogenetic analysis by chromosome painting using DOP-PCR amplified flow-sorted chromosomes. Genes, Chromosomes & Cancer 4: 257–263 (1992).

---

What is claimed is:

1. A sequence independent method of amplifying DNA, comprising:

(a) denaturing a DNA sample;

(b) annealing said DNA with a first primer having random nucleotides at its 3' end and a defined sequence at its 5' end at a temperature effective to allow the formation of a DNA-primer hybrid;

(c) incubating said DNA-primer hybrid with a first DNA polymerase to synthesize a DNA product; and (d) subjecting said DNA product to PCR amplification using a PCR reaction mixture comprising a heat stable DNA polymerase and a second primer having at its 3' end the sequence of said first primer and an additional 5' overhang that is not part of the first primer.

2. The method of claim 1 wherein steps (a) and (b) are repeated.

3. The method of claim 1 wherein steps (a) and (b) are repeated at least 3 times.

4. The method of claim 1 wherein denaturing is achieved by heating said DNA sample to a temperature of between about 94° C. and about 97° C.

5. The method of claim 1 wherein the temperature effective to allow formation of the DNA-primer hybrid is between about 4° C. and about 13° C.

6. The method of claim 1 wherein said first DNA polymerase has primer displacement activity.

7. The method of claim 1 wherein said first DNA polymerase is T7 DNA polymerase.

8. The method of claim 1 wherein the incubating is between about 13° C. and about 37° C.

9. The method of claim 1 wherein the temperature in step (b) is about 37° C.

10. The method of claim 1 wherein the reaction mixture volume of step (d) is about 10 to 100 fold greater than the reaction mixture volume of step (c).

11. The method of claim 1 wherein the second DNA polymerase is Taq DNA polymerase.

12. The method of claim 1 wherein step (d) comprises a first PCR step with denaturation at about 94° C., annealing at about 45° C., ramping to about 72° C. and synthesis at about 72° C. and a second PCR step with denaturation at about 94° C., annealing at about 56° C., and synthesis at about 72° C.

13. The method of claim 12 wherein the low stringency PCR step comprises formation of a DNA-primer hybrid at a temperature of between about 40° C. and about 50° C.

14. The method of claim 12 wherein the second PCR step comprises formation of a DNA-primer hybrid at a temperature that is higher than the temperature of the first step up to about 72° C.

15. The method of claim 12 wherein the first PCR step is repeated about 5 times and the second PCR step is repeated about 30–33 times.

16. The method of claim 1 wherein said first primer comprises about 4 to about 8 random nucleotides at the 3' end.

17. The method of claim 16 wherein the first primer has SEQ ID NO. 1.

18. The method of claim 1 wherein the second primer is 15–28 nucleotides in length.

19. The method of claim 1 wherein the 3' end of the second primer has a sequence substantially the same as the defined sequences of the first primer.

20. The method of claim 19 wherein the second primer has sequence SEQ ID NO. 2.

21. The method of claim 1 wherein the first or second primers include a single or multiple restriction enzyme recognition site.

22. The method of claim 1 wherein the DNA sample is obtained from microdissected chromosomal material.

23. The method of claim 1 wherein the DNA sample is YAC DNA, a gel purified DNA segment, genomic DNA or a cDNA.

24. The method of claim 23 comprising labeling the amplified DNA with a fluorescent label.

* * * * *